United States Patent
Snell et al.

(10) Patent No.: US 11,911,535 B2
(45) Date of Patent: *Feb. 27, 2024

(54) IMPLANTABLE MEDICAL DEVICE WITH THERMOPLASTIC COMPOSITE BODY AND METHOD FOR FORMING THERMOPLASTIC COMPOSITE BODY

(71) Applicant: HAPPE Spine LLC, Grand Rapids, MI (US)

(72) Inventors: Douglas Snell, Overland Park, KS (US); Robert Ball, West Olive, MI (US); Ryan K. Roeder, Granger, IN (US)

(73) Assignee: HAPPE Spine LLC, Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,816

(22) Filed: Mar. 16, 2023

(65) Prior Publication Data
US 2023/0218805 A1    Jul. 13, 2023

Related U.S. Application Data

(63) Continuation of application No. 16/817,470, filed on Mar. 12, 2020, now Pat. No. 11,607,476.
(Continued)

(51) Int. Cl.
*A61L 27/56* (2006.01)
*A61L 27/48* (2006.01)
(Continued)

(52) U.S. Cl.
CPC .......... *A61L 27/56* (2013.01); *A61F 2/30771* (2013.01); *A61L 27/48* (2013.01);
(Continued)

(58) Field of Classification Search
CPC ...... A61L 27/56; A61L 27/48; A61L 2430/02; A61L 2430/38; A61F 2/30771;
(Continued)

(56) References Cited

U.S. PATENT DOCUMENTS

| 7,758,882 B2 | 7/2010 | Roeder et al. |
| 7,879,093 B2 | 2/2011 | Wei et al. |

(Continued)

FOREIGN PATENT DOCUMENTS

| WO | 2001054746 | 8/2001 |
| WO | 2005047467 | 5/2005 |

(Continued)

OTHER PUBLICATIONS

Chawla, Krishan K., Composite Materials, Science and Engineering, Second Edition, 1998, 1987 Springer Science + Business Media, Inc., United States.
(Continued)

*Primary Examiner* — Blessing M Fubara
(74) *Attorney, Agent, or Firm* — McNees Wallace & Nurick LLC

(57) ABSTRACT

An implantable medical device is disclosed comprising a thermoplastic composite body having anterior, first lateral, second lateral, posterior, superior, and inferior surfaces, and at least one dense portion and at least one porous portion which are integrally formed. The at least one dense portion is formed of a first thermoplastic polymer matrix that is essentially non-porous, and which is continuous through a thickness dimension from the superior surface to the inferior surface. The at least one porous portion is formed of a porous thermoplastic polymer scaffold having a second thermoplastic polymer matrix which is continuous through the thickness dimension. A method for forming the thermoplastic composite body is disclosed comprising disposing a
(Continued)

first powder mixture in a first portion of a mold, disposing a second powder mixture in a second portion of the mold, simultaneously molding the first powder mixture and the second powder mixture, and leaching porogen.

20 Claims, 14 Drawing Sheets

Related U.S. Application Data

(60) Provisional application No. 62/817,111, filed on Mar. 12, 2019.

(51) Int. Cl.

| | | |
|---|---|---|
| *A61F 2/30* | (2006.01) | |
| *B29C 43/02* | (2006.01) | |
| *B29K 101/12* | (2006.01) | |
| *B29L 31/00* | (2006.01) | |
| *B29K 105/00* | (2006.01) | |

(52) U.S. Cl.
CPC .... *B29C 43/02* (2013.01); *A61F 2002/30006* (2013.01); *A61F 2002/30011* (2013.01); *A61F 2002/30065* (2013.01); *A61F 2002/30593* (2013.01); *A61F 2002/30784* (2013.01); *A61F 2002/30957* (2013.01); *A61L 2430/02* (2013.01); *A61L 2430/38* (2013.01); *B29K 2101/12* (2013.01); *B29K 2105/251* (2013.01); *B29L 2031/753* (2013.01)

(58) Field of Classification Search
CPC .. A61F 2002/30006; A61F 2002/30011; A61F 2002/30593; A61F 2002/30784; B29C 43/02; B29K 2101/12; B29K 2105/251; B29L 2031/753
See application file for complete search history.

(56) References Cited

U.S. PATENT DOCUMENTS

| | | |
|---|---|---|
| 7,972,628 B2 | 7/2011 | Ratner et al. |
| 8,318,193 B2 | 11/2012 | Ratner et al. |
| 8,383,024 B2 | 2/2013 | Croteau |
| 8,530,560 B2 | 9/2013 | Kerr et al. |
| 8,609,127 B2 | 12/2013 | Savage-Erickson |
| 8,729,150 B2 | 5/2014 | Jarman-Smith et al. |
| 8,829,096 B2 | 9/2014 | Jarman-Smith |
| 11,607,476 B2 * | 3/2023 | Snell ....................... A61F 2/447 |
| 2003/0031698 A1 | 2/2003 | Roeder |
| 2003/0125739 A1 * | 7/2003 | Bagga ................... A61F 2/4455 606/907 |
| 2005/0100578 A1 | 5/2005 | Schmid |
| 2005/0251267 A1 | 11/2005 | Winterbottom |
| 2007/0041952 A1 | 2/2007 | Guilak et al. |
| 2008/0161927 A1 | 7/2008 | Savage et al. |
| 2008/0206297 A1 | 8/2008 | Roeder |
| 2009/0099661 A1 | 4/2009 | Bhattacharya et al. |
| 2009/0164023 A1 | 6/2009 | Devine |
| 2009/0317766 A1 | 12/2009 | Heidenau |
| 2010/0016985 A1 | 1/2010 | Rabiei |
| 2010/0129416 A1 | 5/2010 | Murphy et al. |
| 2010/0145393 A1 | 6/2010 | Fallin et al. |
| 2010/0168798 A1 | 7/2010 | Clineff |
| 2010/0211183 A1 | 8/2010 | Chi |
| 2010/0298937 A1 | 11/2010 | Laurencin et al. |
| 2010/0317039 A1 | 12/2010 | Salk |
| 2011/0012280 A1 * | 1/2011 | Deslauriers ......... B29C 44/1214 264/45.7 |
| 2011/0022180 A1 | 1/2011 | Melkent et al. |
| 2011/0022181 A1 | 1/2011 | Kasahara et al. |
| 2011/0035018 A1 | 2/2011 | Deffenbaugh et al. |
| 2011/0045087 A1 | 2/2011 | Kerr et al. |
| 2011/0054625 A1 | 3/2011 | Ferko et al. |
| 2011/0151259 A1 | 6/2011 | Jarman-Smith et al. |
| 2011/0189466 A1 | 8/2011 | Jaggi et al. |
| 2011/0230590 A1 | 9/2011 | Jarman-Smth et al. |
| 2012/0101185 A1 | 4/2012 | Valentine et al. |
| 2012/0323339 A1 | 12/2012 | Olalde Graells |
| 2013/0066320 A1 | 3/2013 | Jarman-Smith et al. |
| 2013/0171443 A1 | 7/2013 | Morrissette et al. |
| 2014/0035201 A1 | 2/2014 | Jarman-Smith et al. |
| 2014/0107299 A1 | 4/2014 | Valentine et al. |
| 2014/0200466 A1 | 7/2014 | Serano et al. |
| 2014/0228497 A1 | 8/2014 | Jarman-Smith |
| 2014/0343707 A1 | 11/2014 | Serano et al. |
| 2017/0209283 A1 * | 7/2017 | Vickers ................ A61F 2/4611 |

FOREIGN PATENT DOCUMENTS

| | | |
|---|---|---|
| WO | 2008106625 | 9/2008 |
| WO | 2013076493 | 5/2013 |
| WO | 2014068285 | 5/2014 |

OTHER PUBLICATIONS

Rotel, M., et al., Preadhesion Laser Surface Treatment of Carbon Fiber Reinforced PEEK Composite; A. BUchman & H. Dodiuk; Dec. 1995.

Kausch, H., et al., Advanced Thermoplastic Composites: Characterization and Processing; Oxford University Press, USA, 1993, p. 341.

Kane et al., "Effects of the reinforcement morphology on the fatigue properties of hydroxyapatite reinforced polymers," J. Mech. Behav. Biomed. Mater., 1 [3] 261-268 (2008).

Dalby, M.J. et al., Surface topography and HA filler volume effect on primary human osteoblasts in vitro., Bonfield W. J. Mater Sci Mater Med. Dec. 2000; 11(12): 805-10.

D.W. Grant, "Reduced Burst Release of Bioactive rhBMP-2 from a Three-Phase Composite Scaffold, " M.S. Thesis, University of Toronto, 2010.

Lickorish, D., et al., A three-phase, fully resorbable, polyester/calcium phosphate scaffold for bone tissue engineering: Evolution of scaffold design; Elsevier, Science direct, Biomaterials 28 (2007) 1495-1502, Canada.

Kurtz, S., et al., PEEK biomaterials in trauma, orthopedic, and spinal implants; Elsevier, Science Direct, Biomaterials 28 (2007) 1845-4869.

Shaug et al.; Bone formation by three-dimensional stromal osteoblast culture in biodegradable polymer scaffolds; Journal of Biomedical Materials Research, vol. 36, 17-28 (1997).

Thomson et al.; Hydroxyapatite fiber reinforced poly(a-hydroxy ester) foams for bone regeneration; Biomaterials 19 (1998) 1935-1943.

Post, M.J. "Design and Manufacture of Polymer Osseointegrative Scaffolds," Graduate Program in Aerospace and Mechanical Engineering, Notre Dame, IN, 2007.

Schmid, S.R. et al., "A Manufacturing Framework for Biomimetic Porous Metals," Department of Aerospace and Mechanical Engineering, University of Note Dame, IN., Transaction of NAMRI/SME, pp. 183-188, vol. 37, 2009.

Tan, K.H. et al., "Fabrication and characterization of three-dimensional poly(ether-ether-ketone)/-hydroxyapatite biocomposite scaffolds using laser sintering," 2004, pp. 183-194, Proc. IMechE., vol. 219 Part H:J, Engineering in medicine, 2004.

Von Wilmowsky, C., et al., "Effects of bioactive glass and B-TCP containing three-dimensional laser sintered polyetheretherketone composites on osteoblasts in vitro," Wiley Periodicals, INc., Jr. Biomed Master Res 87A: 896-902, 2008.

Duan, B., et alk., "Three-dimensional nanocomposite scaffolds fabricated via selective laser sintering for bone tissue engineering," Acta Biomaterials 6 (2010), 4495-4505, Elsevier Ltd.

Evans, N.T., et al. "High-strength, surface-porous polyether-ether-ketone for load-bearing orthopedic implants," Acta Biomaterialia 13 (2015), 159-167, Elsevier Ltd.

(56) References Cited

OTHER PUBLICATIONS

Siddiq, A.R., et al., "Porous poly-ether ether ketone (PEEK) manufactured by a novel powder route using near-spherical salt bead porogens: Characterisation and mechanical properties," Materials Science and Engineering C 47 (2015), 180-0188, 2014, Elsevier B.V.

Evans, N.T., et al., "Impact of surface porosity and topography on the mechanical behavior of high strength biomedical polymers," Journal of the Mechanical Behavior of Biomedical Materials 59 (2016), 459-473, 2016, Elsevier Ltd.

P. Moreno, Femtosecond laser ablation of carbon reinforced polymers, Applied Surface Science 252 (2006), 4110-4119; Elsevier B.V.

R. Roeder, Porous and Bioactive PEEK Implants for Interbody Spinal Fusion, Advanced Materials & Processes/Oct. 2009.

R. Roeder, Hydroxyapatite-Reinforced Polymer Biocomposites for Synthetic Bone substitues, 2008, march + JOM, pp. 38-45.

G. Converse, Mechanical properties of hydroxyapatite whisker reinforced polyethererketoneketone composite scaffolds, Journal of the Medhcanical Behavior of Biomedical Materials, S 2 (2009), 627-635, Elsevier B.V.

G. Converse, Hydroxyapatite whisker-reinforced polyetherketoneketone bone ingrowth scaffolds, Acta Biomaterialia 6 (2010), 856-863, Elsevier B.V.

J. Deuerling, Micromechanical Model for the Orthotropic Elastic Constants of Polyetheretherketone Composites Considering the Orientation Distribution of the Hydroxyapatite Whisker Reinforcements, Journal of Engineering Materials and Technology, Jan. 2012, vol. 134, pp. 010906-1-8.

R. Roeder, Bioactive Polyaryletherketone Composites, PEEK Biomaterials Handbook, 2012, Chapter 11, pp. 163-179, Elsevier B.V.

T. Conrad, Effects of the mold temperature on the mechanical properties and crystallinity of hydroxyapatite whisker- reinforced polyetheretherketone scaffolds, Journal of Biomedical Materials Research b: Applied Biomaterials, May 2013, vol. 101B, issue 4, pp. 576-583, Wiley Periodicals, Inc.

M. Meagher, Surface Adsorption of rhBMP-2 to Hydroxyapatite Reinforced PEEK Scaffolds, ABSTRACT; Department of Aerospace and Mechanical Engineering, Bioengineering Graduate Program, University of Notre Dame.

International Search Report issued for Application No. PCT/US2019/051704 dated Jan. 30, 2020.

\* cited by examiner (a)

(b)

(c)

IMPLANTABLE MEDICAL DEVICE WITH THERMOPLASTIC COMPOSITE BODY AND METHOD FOR FORMING THERMOPLASTIC COMPOSITE BODY

CROSS-REFERENCE TO RELATED APPLICATIONS

This application is a continuation of, and clams the benefit of, U.S. patent application Ser. No. 16/817,470, entitled "Implantable Medical Device with Thermoplastic Composite Body and Method for Forming Thermoplastic Composite Body," which was filed on Mar. 12, 2020 and which claims the benefit of, and priority to, U.S. Provisional Application No. 62/817,111, entitled "Variable Density Implants," which was filed on Mar. 12, 2019, both of which are hereby incorporated by reference in their entirety.

FIELD

The present disclosure relates generally to composite biomedical implants having regions with varying porosity, and more particularly composite spinal implants having regions that are relatively porous and regions that are relatively dense, the varied porosity being selected to enhance bony ingrowth into the implant while providing mechanical support to maintain distraction of vertebrae.

BACKGROUND

Interbody spinal fusion is used to alleviate pain caused when a herniated, bulging, or flattened intervertebral disc impinges on the spinal cord or nerve root. The disc and vertebral endplates are re-moved and an interbody fusion implant is inserted in the disc space to restore vertebral height, promote fusion of bone tissue between adjacent vertebrae, and, thus, mechanically stabilize the spine. Generally, the choices for spinal implants fall largely into metallic, polymeric, carbon fiber based and ceramic. Polyaryletherketone (PAEK) and bioactive PAEK composites for biomedical devices present several advantageous properties. PAEK polymers are generally biocompatible, bioinert, and radiolucent, and they exhibit a high strength and similar compliance to bone. One example of PAEK polymers used for biological implants is polyetheretherketone (PEEK). PEEK implants have many attractive characteristics, in particular for spinal surgeons and patients. Because of the radiolucency of PAEK composites, implants formed with PEEK allow post-operative radiographic assessment of fusion, which is problematic with metallic implants due to relatively high x-ray attenuation of titanium. PEEK also exhibits a modulus of elasticity similar to bone, enhancing load transfer and osteogenic signals to tissue in the implant, and reducing the likelihood of vertebral subsidence compared to alternatives formed with metals and ceramics. Porous PEEK provides surface area and architecture to support more extensive bony tissue ingrowth into the porous implant surfaces. Of particular interest are porous PEEK materials that are reinforced with calcium phosphate, and in some examples, calcium phosphate particles selected from anisometric hydroxyapatite particles. These materials have been reported to provide bioactivity for enhanced bony ingrowth into the implant by the exposure of the anisometric hydroxyapatite particles on the surfaces of and extending within the pore voids. Despite the advantages of the foregoing described implant technologies, there remains a need in the art for implants that include the advantageous features of PAEK materials provided in an implant construct that is adapted to spinal anatomy to achieve extensive bony ingrowth into the implant and provide mechanical properties that discourage stress shielding and have strength properties to handle the physiological loads during fusion.

BRIEF DESCRIPTION OF THE INVENTION

In one exemplary embodiment, an implantable medical device comprises a thermoplastic composite body. The thermoplastic composite body includes an anterior surface of the thermoplastic composite body, a first lateral surface of the thermoplastic composite body, a second lateral surface of the thermoplastic composite body, a posterior surface of the thermoplastic composite body, a superior surface of the thermoplastic composite body, an inferior surface of the thermoplastic composite body, at least one dense portion, and at least one porous portion. The at least one dense portion is formed of a thermoplastic polymer matrix that is essentially non-porous, and which is continuous through a thickness dimension from the superior surface of the thermoplastic composite body to the inferior surface of the thermoplastic composite body. The at least one porous portion is formed of a porous thermoplastic polymer scaffold which is continuous through the thickness dimension from the superior surface of the thermoplastic composite body to the inferior surface of the thermoplastic composite body. In accordance with the disclosure, the composite has interconnected pores.

In another exemplary embodiment, an implantable medical device includes a thermoplastic composite body. The thermoplastic composite body includes an anterior surface of the thermoplastic composite body, a first lateral surface of the thermoplastic composite body, a second lateral surface of the thermoplastic composite body, a posterior surface of the thermoplastic composite body, a superior surface of the thermoplastic composite body, an inferior surface of the thermoplastic composite body, at least one dense portion formed of a first thermoplastic polymer matrix that is essentially non-porous, and which is continuous through a thickness dimension from the superior surface of the thermoplastic composite body to the inferior surface of the thermoplastic composite body, at least one porous portion formed of a porous thermoplastic polymer scaffold, the porous thermoplastic polymer scaffold being formed of a second thermoplastic polymer matrix, the at least one porous portion being continuous through the thickness dimension from the superior surface of the thermoplastic composite body to the inferior surface of the thermoplastic composite body, at least one reinforcement material dispersed throughout the at least one dense portion and the at least one porous portion, and at least one central through cavity extending from the superior surface of the thermoplastic composite body to the inferior surface of the thermoplastic composite body and disposed inward from the anterior surface of the thermoplastic composite body, the first lateral surface of the thermoplastic composite body, the second lateral surface of the thermoplastic composite body, and the posterior surface of the thermoplastic composite body. The at least one porous portion includes at least one porous outer wall disposed along the anterior surface of the thermoplastic composite body, the first lateral surface of the thermoplastic composite body, and the second lateral surface of the thermoplastic composite body, and at least one porous central portion defining an outer boundary of the at last one central through cavity. The at least one dense portion includes at least one dense core disposed between the at least one porous central portion and the at least one porous outer wall, the at least one dense core extending to the posterior surface of the thermoplastic composite body, forming a dense posterior edge, and a plurality of projections extending outward relative to the at least one porous portion from at least one of the superior surface of the thermoplastic composite body or the inferior surface of the thermoplastic composite body. The at least one dense portion defines a closed lateral structural support, and the thermoplastic composite body having the closed lateral structural support is more durable with respect to insertion forces than an otherwise identical comparative thermoplastic composite body lacking the closed lateral structural support. The at least one dense portion and the at least one porous portion are integrally formed such that the thermoplastic composite body is a single continuous article free of adhesive and mechanical joints between the at least one dense portion and the at least one porous portion.

In another exemplary embodiment, a method for forming a thermoplastic composite body comprises disposing a first powder mixture in a first portion of a mold, the first powder mixture including a first thermoplastic polymer powder. The first powder mixture is compacted to densify the first powder mixture at a first pressure. A second powder mixture is disposed in a second portion of the mold, the second powder mixture including a second thermoplastic polymer powder and a porogen material. The second powder mixture is compacted to densify the second powder mixture at a second pressure. The first powder mixture and the second powder mixture are simultaneously molded at a molding temperature above room temperature and at a final molding pressure. The simultaneous molding forms at least one dense portion having a first thermoplastic polymer matrix that is essentially non-porous from the first powder mixture and forms at least one proto-porous portion having a second thermoplastic polymer matrix from the second powder mixture. The porogen material is leached from the at least one proto-porous portion, forming at least one porous portion having a porous thermoplastic polymer scaffold that is continuous from the at least one proto-porous portion. The thermoplastic polymer scaffold includes the second thermoplastic polymer matrix. The simultaneous molding and the leaching integrally form the at least one dense portion and the at least one porous portion as a single continuous article free of adhesive and mechanical joints between the at least one dense portion and the at least one porous portion. In some embodiments, the method may involve use of more than two powder mixtures.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Wherever possible, the same reference numbers will be used throughout the drawings to represent the same parts.

DETAILED DESCRIPTION OF THE INVENTION

Figure 1:
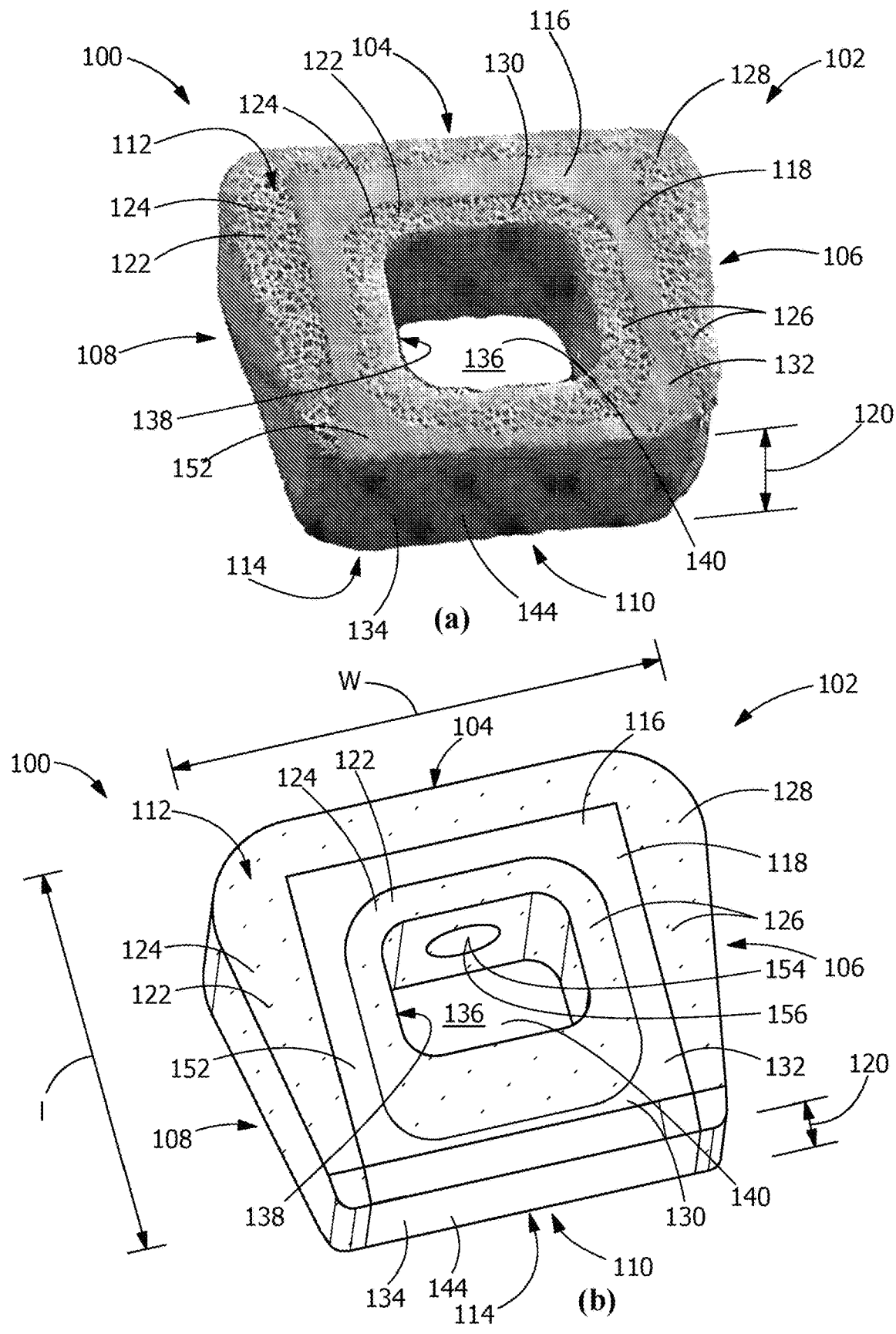
FIG. 1 is a perspective view in photographic (a) and schematic (b) form of an implantable medical device, according to an embodiment of the disclosure.
Figure 2:
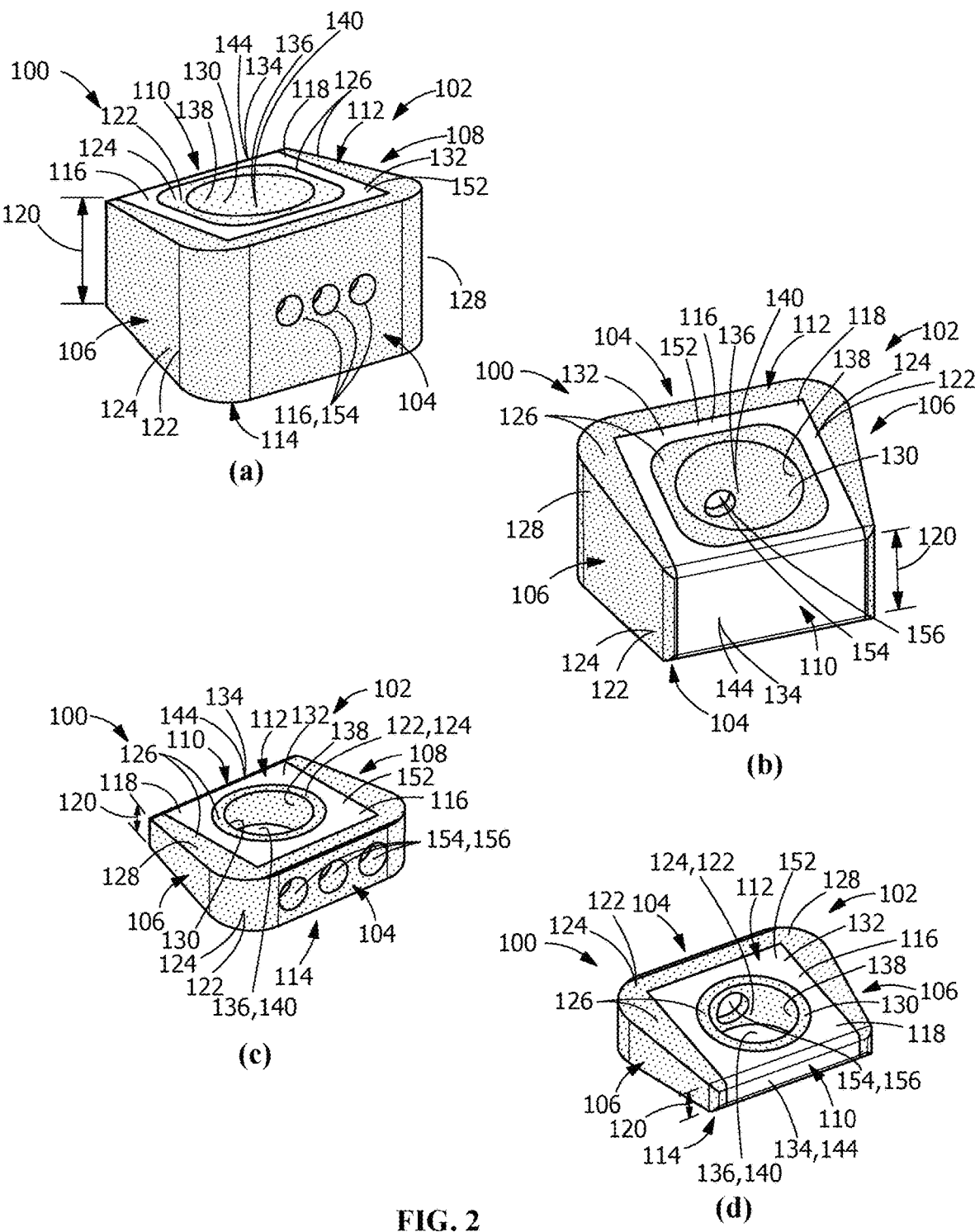
FIG. 2 shows alternate anterior (a) and posterior (b) perspective views of a thick implantable medical device and anterior (c) and posterior (d) perspective views of a thin implantable medical device (relative to FIG. 1), according to embodiments of the disclosure.
Figure 3:
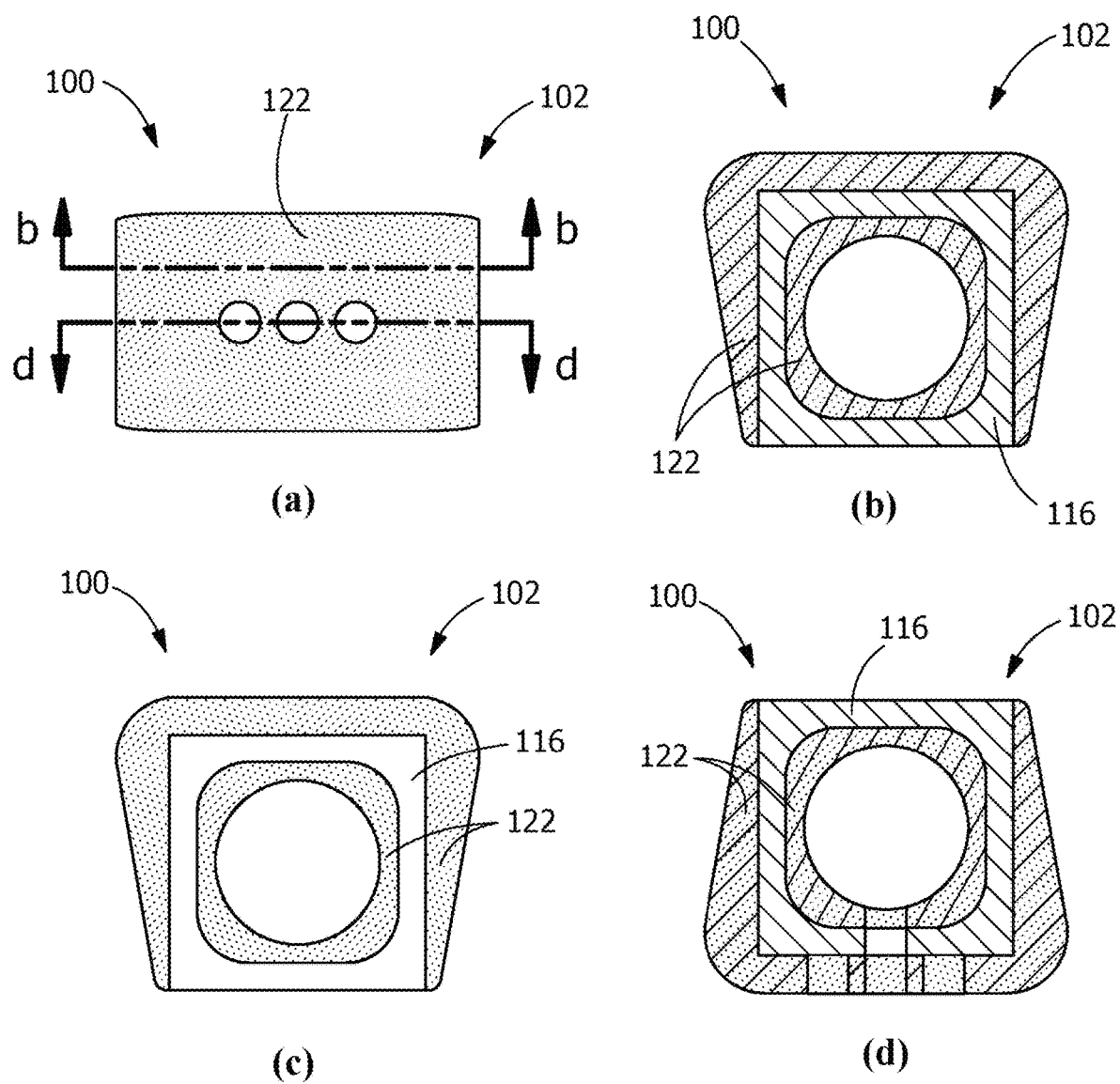
FIG. 3 shows anterior (a), superior (b), and first cross-sectional (c) and second cross-sectional (d) views of an implantable medical device, according to an embodiment of the disclosure.
Figure 4:
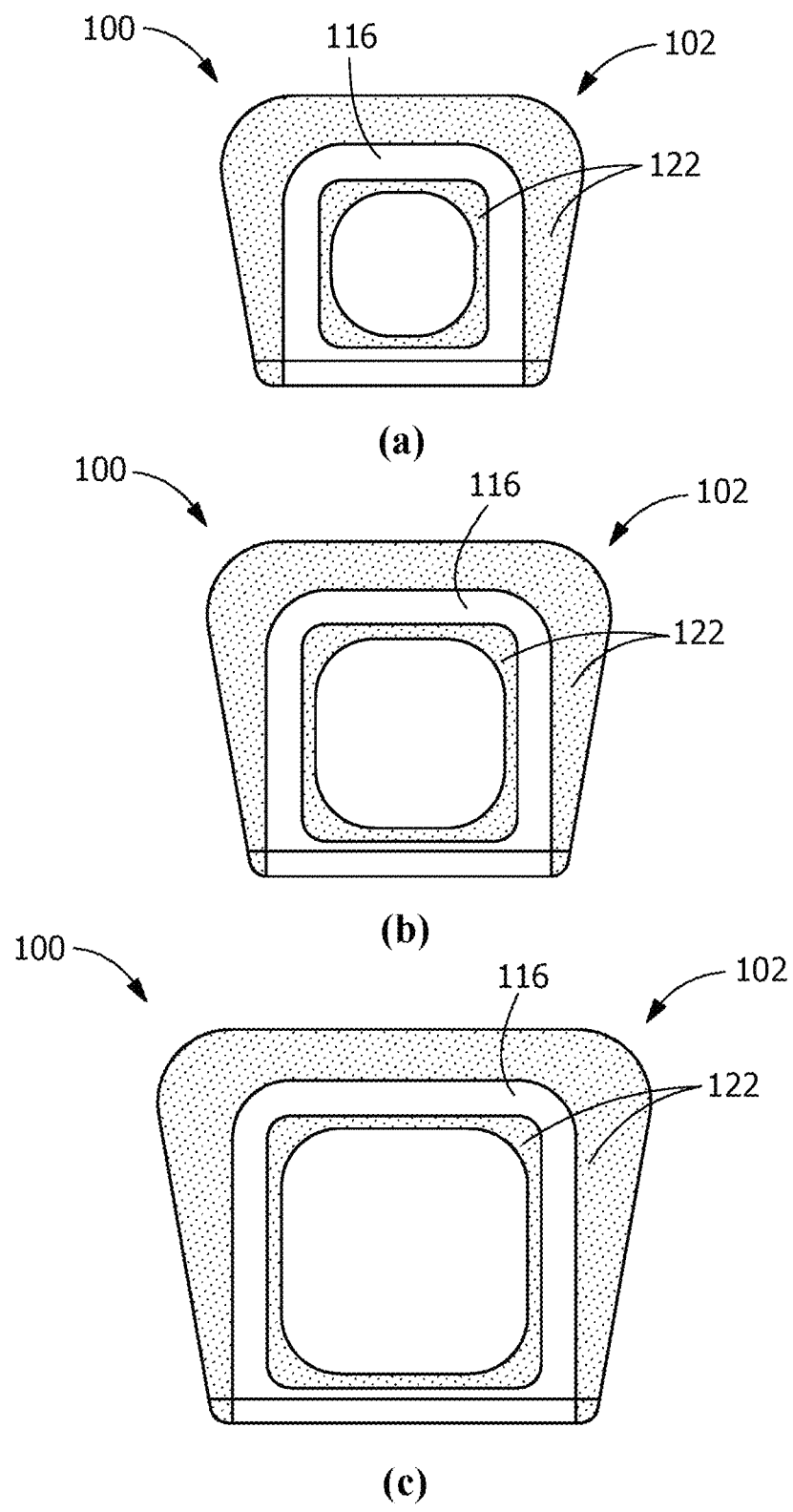
FIG. 4 shows small (a), medium (b), and large (c) sizes of the embodiment of an implantable medical device as shown in FIG. 1, according to an embodiment of the disclosure.

The general inventive concepts will now be described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

Provided are medical device implants which may be bioactive, particularly for use in the spine, that address the mechanical and biological requirements for maximizing integration of the implant during bony fusion between vertebrae. The implants take advantage of dense and porous reinforced polymer wherein the relative density of portions of the device may be varied to one or more of: match mechanical properties of the vertebral bodies or bone tissue which is to be contacted by the implant; provide anatomically desirable distraction between vertebrae; provide mechanical strength to support and maintain balance in the sagittal plane; minimize subsidence; and provide for optimal osteointegration.

Implants as provided include a combination of dense and porous regions that influence the overall stiffness of the implant, wherein stiffness may be determined by the ratio of cross-sectional area (normal to direction of loading) of the portions of the implant that include porous and dense material. The ratio of cross-sectional area (normal to direction of loading) and placement of the dense and porous portions may be configured to provide an implant that can be matched to the mechanical properties of the vertebral bodies or bone tissue which it is intended to contact, both in overall implant stiffness, and in cross-sectional location of the relatively stiffer dense portions and the relatively flexible porous portions. In some embodiments, one or more of the dense and porous portions comprise one or more reinforcement particles which may be exposed on the surface of pores within at least some of the porous portions. In some particular embodiments, the implant is formed of a polymer selected from PAEK polymers, and include reinforcement particles in at least some portions, wherein the reinforcement particles comprise calcium phosphate compositions known to be bioactive.

Advantages realized according to the various embodiments of implantable devices that are adapted for use in the spine, as described herein, include the following: dense portions, for example those that comprise hydroxyapatite reinforced PEEK, provide biomechanical support only where it is needed; porous regions, for example those that comprise porous hydroxyapatite reinforced PEEK, enable bone ingrowth for osteointegration where most beneficial, for example on the inner implant surface in the graft window for graft incorporation to the implant and/or the anterior outer implant surface to support sentinel-sign bone growth; interconnected porosity provides biological pathway from vertebrae to vertebrae, through the implant to promote thorough osteo-conductivity; in some embodiments, exposed reinforcements, for example, any bioactive reinforcement, and in some specific examples, hydroxyapatite whiskers, enhance bioactivity of the implant; porous fusion anteriorly supports sentinel-sign bone growth; porous fusion laterally maximizes the breadth of bone growth stabilization as well as adds a conformable material in a region where the bony geometry is less planar; dense material on the posterior outer implant surface discourages bone growth and maximizes mechanical support to maintain foraminal height; threaded inserter hole transmits inserter impaction to a load bearing frame; keystone footprint allows for maximal endplate area contact while maintaining clearance for nerve pathways. It will be appreciated that in some embodiments, the thermoplastic polymer may be a polymer other than PEEK and other than a PAEK polymer. It will also be appreciated that in some embodiments, the thermoplastic polymer may not include any reinforcement material within any one or more of the dense and porous portions, and that in yet other embodiments, the thermoplastic polymer may contain one or a combination of reinforcement materials that may or may not comprise calcium phosphate, hydroxyapatite or hydroxyapatite whiskers. In some examples, other bioactive reinforcements that do not comprise calcium phosphate may be selected.

Human bone tissues exhibit substantial variation in mechanical properties depending on the tissue density and microstructure. The properties are highly dependent on anatomic location and apparent density of the measured specimen. For example, cortical bone, such as in a thin outer wall of a vertebral body, has a relative porosity on the order of about 5-15%, and a trabecular bone, such as in the central majority or marrow cavity of a vertebral body, has a porosity on the order of about 75-95%. Due to the highly significant porosity differences, trabecular bone exhibits significantly lower effective mechanical properties compared to cortical bone. Therefore, depending on the application, synthetic composite materials for use as scaffolds and/or spinal fusion implants or other implant devices should possess the mechanical properties exhibited by cortical bone or trabecular bone, but must also have effective porosity to promote bone ingrowth.

To avoid the mechanical mismatch problems, such as stress shielding, it is desirable to substantially match or mimic the mechanical properties (e.g., elastic modulus) of the adjacent and/or substituted bone tissue. Several factors may be varied during the manufacturing of the implant device, and/or composite material and scaffold of the implant device, to tailor the mechanical properties including the ratio of the cross-sectional area of dense to porous thermoplastic polymer in the implant, the reinforcement volume fraction, aspect ratio, size and orientation; the polymer; and the size, volume fraction, shape and directionality of the porosity. Tailoring the mechanical properties of the implant and/or composite materials and scaffold reduces the likelihood of mechanical mismatch leading to a decreased risk of subsidence, stress shielding, bone resorption and/or subsequent failure of adjacent vertebrae.

Porous polymer scaffolds may be tailored to mimic biological and mechanical properties of bone tissue for implant fixation, synthetic bone graft substitutes, tissue engineering scaffolds, interbody spinal fusion, or other orthopedic applications. An example porous composite material described herein reduces subsidence and/or bone resorption resulting from mechanical mismatch problems between a synthetic scaffold of an implant device and the peri-implant tissue. Additionally, porosity and/or the pore sizes of the example thermoplastic composite are tailorable to specific applications to effectively promote the vascularization and growth of bone in the pores and/or void spaces of the example scaffolds, thereby improving bonding between the scaffolds and peri-implant tissue.

Composite materials or scaffolds may be synthesized or made through a process that enables reinforcement particles to be integrally formed with or embedded within polymer matrices. In this manner, the polymer matrices embedded with the reinforcement material may provide improved material properties (e.g., elastic modulus, fatigue strength, and toughness). The reinforcement particles are also exposed on a surface of the matrices, which promotes bioactivity and/or osteointegration. Additionally, the process provides flexibility to tailor the level of reinforcement particles and porosity for a desired application. For example, a porogen material may be used to vary the porosity, while the pore size is tailored by, for example, sieving the porogen to a desired size. An additional pore tailoring method is to reshape a porogen material from it native shape to one that promotes interparticle contact between porogen particles and thus improved permeability. For example, sodium chloride particles are natively cubic. A process such as passing the particle through an energy source so that is melts and reforms to a shape other than its native cubic shape. Alternative shapes may be fibers, polyhedrals, spheres, spheroids, ellipses, ellipsoids, or any other suitable shape.

By varying the volume fraction of the reinforcement particles and the porosity of the example scaffold, the mechanical properties (e.g., elastic modulus) of the example scaffold of the implant device may be tailored to match those of the adjacent peri-implant bone tissue to reduce mechanical mismatch problems. Reducing mechanical mismatch provides a decreased risk of subsidence, stress shielding, bone resorption, and/or subsequent failure of adjacent peri-implant bone tissue. Additionally, scaffolds may include a significantly high porosity to promote bone ingrowth, while exhibiting significantly higher effective mechanical properties such as, for example, the mechanical properties of trabecular bone.

The example composite materials described herein may be used for applications such as, for example, synthetic bone graft substitutes, bone ingrowth surfaces applied to existing implants, tissue engineering scaffolds, interbody spinal fusion implants, etc. In each of the applications, bone graft materials (e.g., autograft, demineralized bone matrix, and the like) may be incorporated into the central cavity (or "graft space") of the implant to further enhance osteoinduction and/or osteoconduction to promote osteointegration. Carrier materials (e.g., collagen, hydrogels, etc.) containing growth factors, such as bone morphogenetic proteins (BMP), may also be incorporated into the pore space of the scaffold and/or the central cavity (or "graft space") of the implant to further enhance osteoinduction and/or osteoconduction to promote osteointegration.

Referring to FIGS. 1-8, in one embodiment, an implantable medical device 100 includes a thermoplastic composite body 102 having an anterior surface 104 of the thermoplastic composite body 102, a first lateral surface 106 of the thermoplastic composite body 102, a second lateral surface 108 of the thermoplastic composite body 102, a posterior surface 110 of the thermoplastic composite body 102, a superior surface 112 of the thermoplastic composite body 102, an inferior surface 114 of the thermoplastic composite body 102, at least one dense portion 116 formed of a first thermoplastic polymer matrix 118 that is essentially non-porous, and which is continuous through a thickness dimension 120 from the superior surface 112 of the thermoplastic composite body 102 to the inferior surface 114 of the thermoplastic composite body 102, and at least one porous portion 122 formed of a porous thermoplastic polymer scaffold 124, the porous thermoplastic polymer scaffold 124 being formed of a second thermoplastic polymer matrix 126, the at least one porous portion 122 being continuous through the thickness dimension 120 from the superior surface 112 of the thermoplastic composite body 102 to the inferior surface 114 of the thermoplastic composite body 102.

As used herein, "essentially non-porous" indicates a porosity of less than 15 vol. %, whereas "porous" indicates a porosity of at least 15 vol. %. In a further embodiment, the at least one dense portion 116 formed of a first thermoplastic polymer matrix 118 is substantially non-porous, and "substantially non-porous" indicates a porosity of less than 5 vol. %. The at least one porous portion 122 has a modulus of elasticity that is relatively less than the modulus of elasticity of the at least one dense portion 116.

In a further embodiment, the at least one dense portion 116 and the at least one porous portion 122 are integrally formed such that the thermoplastic composite body 102 is a single continuous article free of adhesive and mechanical joints between the at least one dense portion 116 and the at least one porous portion 122, and the first thermoplastic polymer matrix 118 is continuous with the second thermoplastic polymer matrix 126.

The thermoplastic composite body 102 may have a conformation that is generally a disc or block, that may have an overall shape that ranges from generally circular to elliptical, to ovoid, to generally square to generally trapezoidal. With reference in particular to an implant intended for use in the disc space between spinal vertebrae, the thermoplastic composite body 102 is configured with reference to the orientation relative to the posterior, anterior, and lateral aspects of the spine. Thus, when inserted into a disc space between two vertebrae, an anterior surface 104 of the thermoplastic composite body 102 is intended to be oriented at the anterior aspect of the spine, the posterior surface 110 of the thermoplastic composite body 102 is intended to be oriented at the posterior aspect of the spine, and the first lateral surface 106 and the second lateral surface 108 of the thermoplastic composite body 102 is intended to be oriented at the lateral aspects of the spine.

In one embodiment, the thermoplastic composite body 102 has a generally trapezoidal shape defined by a width dimension (w), a length dimension (l), and a thickness dimension 120, with the periphery of the generally trapezoidal shape being defined by the anterior surface 104 of the thermoplastic composite body 102, the first lateral surface 106 of the thermoplastic composite body 102, the second lateral surface 108 of the thermoplastic composite body 102, the posterior surface 110 of the thermoplastic composite body 102, the superior surface 112 of the thermoplastic composite body 102, and the inferior surface 114 of the thermoplastic composite body 102. The anterior surface 104 may be wider than the posterior surface 110 or narrower than the posterior surface 110. The thickness dimension 120 of the thermoplastic composite body 102 may be continuous or varied. The thickness dimension 120 may uniform or varied along the length from the anterior surface 104 to the posterior surface 110. By way of example, the thickness dimension 120 may vary along the length from relatively thicker at the anterior surface 104 to relatively thinner at the posterior surface 110, providing a wedge shape for the thermoplastic composite body 102, or, alternatively the thickness dimension 120 may vary along the length from relatively thinner at the anterior surface 104 to relatively thicker at the posterior surface 110, providing a wedge shape for the thermoplastic composite body 102. The thermoplastic composite body 102 may have any suitable wedge conformation, including, but not limited to a zero to twenty degree wedge shape anterior to posterior to support the lordotic curvature of the spine during the graft healing. These dimensional changes may be combined in any suitable manner to form different embodiments for particular uses.

In another embodiment, the thermoplastic composite body 102 has a generally circular or elliptical shape and the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102 are designated as four quadrants of the circular or elliptical shape. The thickness dimension 120 may be uniform or vary along an axis bisecting each of the anterior surface 104 and the posterior surface 110, or it may vary along the axis bisecting each of the anterior surface 104 and the posterior surface 110 from relatively thicker at the anterior surface 104 to relatively thinner at the posterior aspect 110, or from relatively thinner at the anterior surface 104 to relatively thicker at the posterior aspect 110.

In one embodiment, the at least one porous portion 122 includes at least one porous outer wall 128 disposed along at least one of the anterior surface 104 of the thermoplastic composite body 102, the first lateral surface 106 of the thermoplastic composite body 102, the second lateral surface 108 of the thermoplastic composite body 102, or the posterior surface 110 of the thermoplastic composite body 102. The at least one porous outer wall 128 may include any suitable thickness, including, but not limited to, a thickness of at least 0.5 mm, alternatively at least 1.0 mm, alternatively at least 1.5 mm, alternatively at least 2 mm, alternatively at least 2.5 mm, alternatively at least 3 mm, alternatively at least 3.5 mm, alternatively at least 4 mm.

The at least one porous portion 122 may further include at least one porous central portion 130. In one embodiment, the at least one dense portion 116 includes at least one dense core 132 disposed between the at least one porous central portion 130 and the at least one porous outer wall 128. The at least one porous central portion 130 may include any suitable thickness. In an embodiment, as further described below, having at least one central through cavity 136, the at least one porous central portion may include, but is not limited to, a thickness of at least 0.5 mm, alternatively at least 1.0 mm, alternatively at least 1.5 mm, alternatively at least 2 mm, alternatively at least 2.5 mm, alternatively at least 3 mm, alternatively at least 3.5 mm, alternatively at least 4 mm. In an embodiment lacking at least one central through cavity 136, the at least one porous central portion may include, but is not limited to, a thickness of at least 3 mm, alternatively at least 4 mm, alternatively at least 5 mm, alternatively at least 10 mm, alternatively at least 15 mm, alternatively at least 20 mm, alternatively at least 25 mm, alternatively at least 30 mm, alternatively at least 35 mm, alternatively up to 40 mm.

In one embodiment, the at least one porous outer wall 128 may be disposed along one of, two of, or all three of the anterior surface 104 of the thermoplastic composite body 102, the first lateral surface 106 of the thermoplastic composite body 102, and the second lateral surface 108 of the thermoplastic composite body 102, and the at least one dense core 132 extends to the posterior surface 108 of the thermoplastic composite body 102, forming a dense posterior edge 134. In another embodiment, the at least one porous outer wall 128 may be disposed along each of the anterior surface 104 of the thermoplastic composite body 102, the first lateral surface 106 of the thermoplastic composite body 102, the second lateral surface 108 of the thermoplastic composite body 102, and the posterior surface 108 of the thermoplastic composite body 102, such that that the at least one dense core 132 is contained within the at least one porous outer wall 128.

The thermoplastic composite body 102 may include at least one central through cavity 136 extending from the superior surface 112 of the thermoplastic composite body 102 to the inferior surface 114 of the thermoplastic composite body 102 and disposed inward from the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102. The central through cavity 136 may include any suitable conformation, and may be a bore, a graft space, or a graft window. In one embodiment, the at least one porous portion includes at least one porous central portion 130, and the at least one porous central 130 portion defines an outer boundary 138 of the at least one central through cavity 136.

In another embodiment, the thermoplastic composite body 102 lacks a central through cavity 136 extending from the superior surface 112 of the thermoplastic composite body 102 to the inferior surface 114 of the thermoplastic composite body 102 and disposed inward from the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102.

The at least one dense portion 116 may extend along at least one of the anterior surface 104 of the thermoplastic composite body 102, the first lateral surface 106 of the thermoplastic composite body 102, the second lateral surface 108 of the thermoplastic composite body 102, or the posterior surface 110 of the thermoplastic composite body 102, forming at least one dense edge 144. In one embodiment, the at least one dense portion 116 extends along at least one of the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102, forming at least one dense outer wall 146, with the at least one porous portion 122 being disposed inward of the at least one dense outer wall 146.

The at least one dense portion 116 may define a closed lateral structural support 152. A thermoplastic composite body 102 having the closed lateral structural support 152 may be more durable with respect to insertion forces than an otherwise identical comparative thermoplastic composite body 102 lacking the closed lateral structural support 152.

Figure 5:
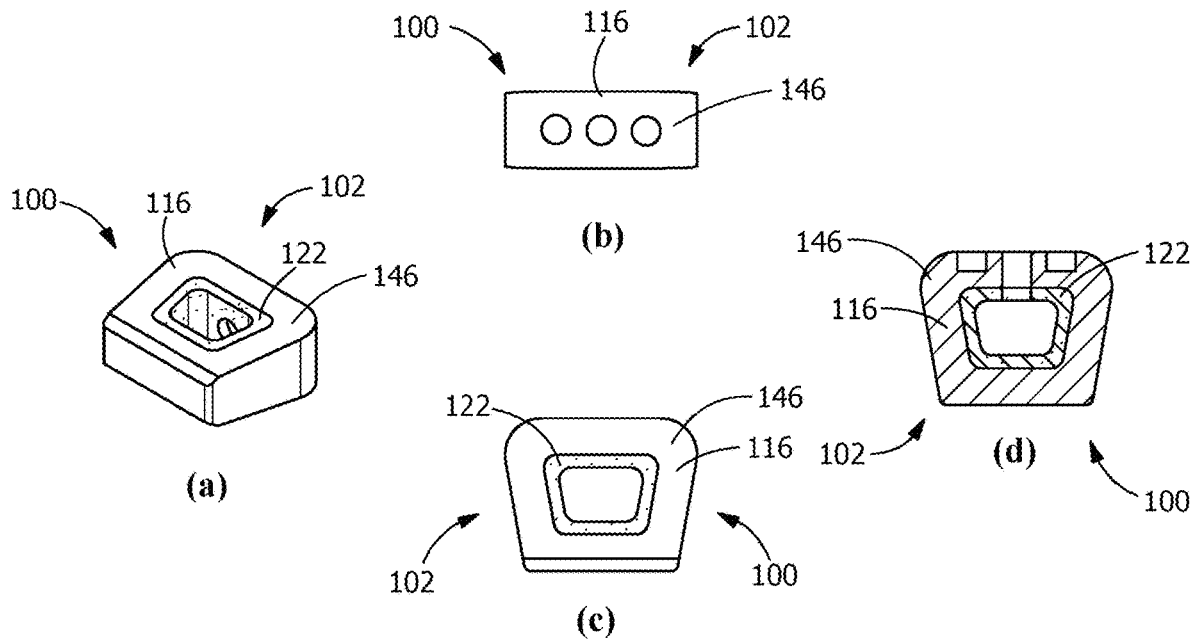
FIG. 5 shows, in alternate views, posterior perspective view (a), an anterior view (b), and superior view (c), and a cross-sectional view (d) of an embodiment of an implantable medical device having dense structural regions on all exterior walls and a porous region lining only the central through cavity, according to an embodiment of the disclosure.

Referring to FIG. 5, in one embodiment the thermoplastic composite body 102 is trapezoidal wedge and includes a central through cavity 136 with a porous central portion 130 defining a boundary of the central through cavity 136. This thermoplastic composite body 102 lacks a porous outer wall 128 such that each of the anterior surface 104 the first lateral surface 10, the second lateral surface 108, and the posterior surface 110 is formed by the at least one dense portion 116.

Figure 6:
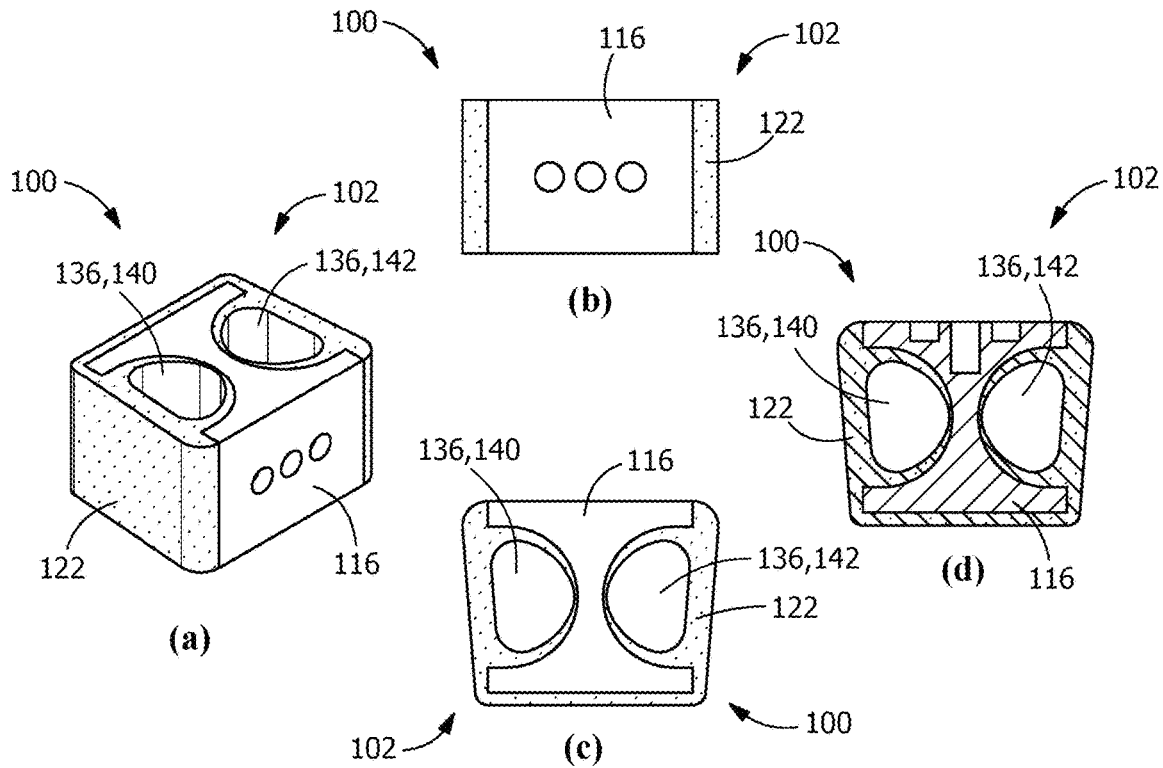
FIG. 6 shows, in alternate views, perspective view (a), an anterior view (b), and superior view (c), and a cross-sectional view (d) of an embodiment of an implantable medical device having two central through cavities, according to an embodiment of the disclosure.
Figure 7:
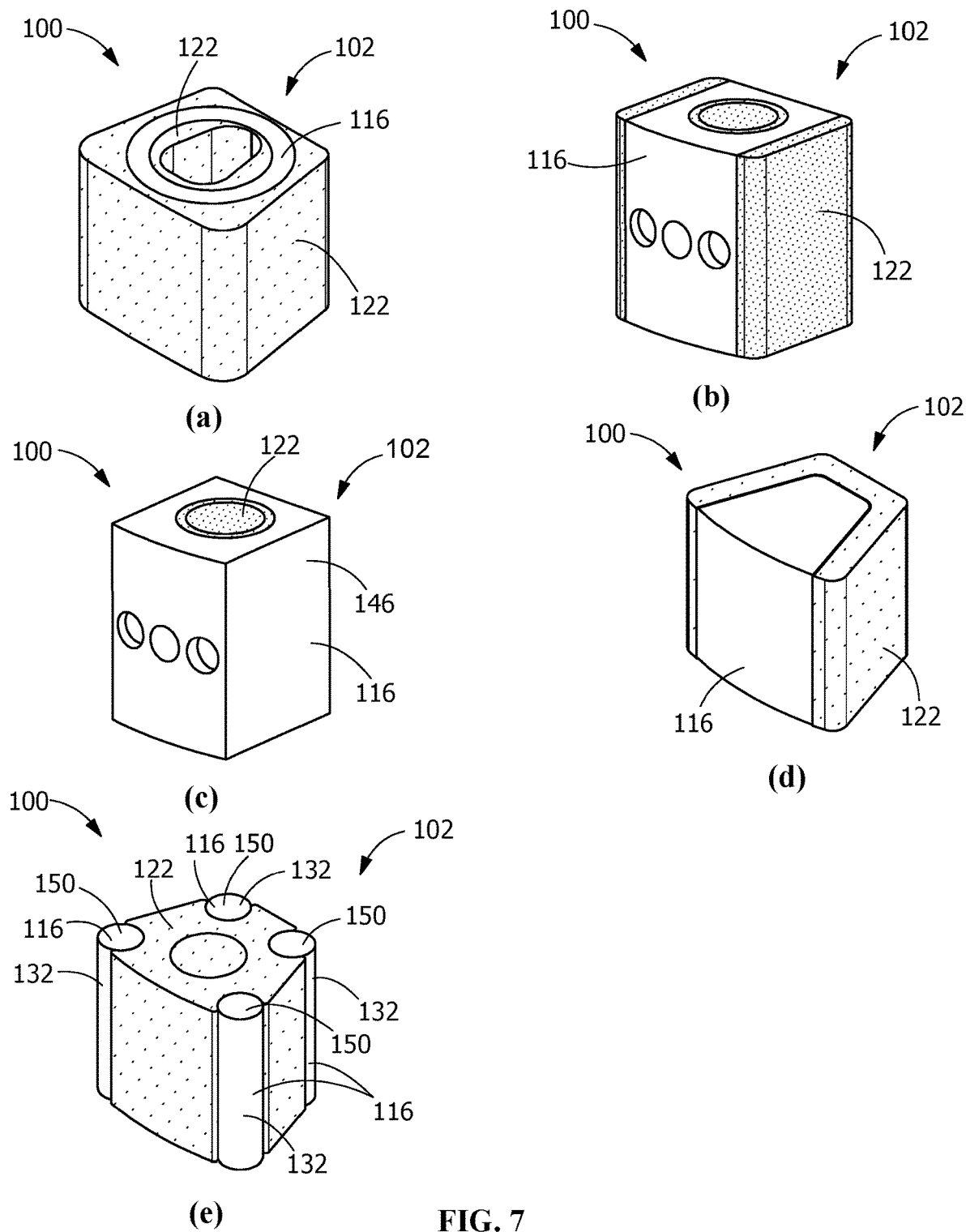
FIG. 7 shows different embodiments of an implantable medical device having a cylindrical dense structural region (a), opposing lateral porous outer walls (b), cylindrical porous portion surrounding a center through cavity (c), a wedge-shaped dense structural region (d), and four cylindrical dense structural regions (e), according to embodiments of the disclosure.

Referring to FIG. 6, in one embodiment, the at least one central through cavity 136 includes a first central through cavity 140 and a second central through cavity 142, and the at least one dense portion 116 extends along the posterior surface 110 of the thermoplastic composite body 102, and extends from the posterior surface 110 of the thermoplastic composite body 102 between the first central through cavity 140 and the second central through cavity 142, and toward the anterior surface 104 of the thermoplastic composite body 102 such that the at least one dense portion 116 is disposed between the first central through cavity 140 and the anterior surface 104 of the thermoplastic composite body 102, and is further disposed between the second central through cavity 142 and the anterior surface 104 of the thermoplastic composite body 102. This continuous dense linkage extending between the first central through cavity 140 and the second central through cavity 142 along a direction from the anterior surface 104 to the posterior surface 110 which connects the at least one dense portion 116 extending along the posterior surface 110 and the at least one dense portion 116 further extending between the first central through cavity 140 and the anterior surface 104 and between the second central through cavity 142 and the anterior surface 104, may also provide increased durability with respect to insertion forces than an otherwise identical comparative thermoplastic composite body 102 lacking the extension of the at least one dense portion 116 between the first central through cavity 140 and the second central through cavity 142.

Referring to FIG. 7(a), in one embodiment the thermoplastic composite body 102 includes a central through portion 136 defined by a porous central portion 130, a circular dense core 132, and has a porous outer wall 128 along each of the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102.

Referring to FIG. 7(b), in one embodiment the thermoplastic composite body 102 includes a central through portion 136 defined by a porous central portion 130, and has a porous outer wall 128 along the first lateral surface 106 of the thermoplastic composite body 102 and the second lateral surface 108 of the thermoplastic composite body 102, and a dense edge 144 along the anterior surface 104 of the thermoplastic composite body 102 and the posterior surface 110 of the thermoplastic composite body 102.

Referring to FIG. 7(c), in one embodiment the thermoplastic composite body 102 having a cuboid block (rather that wedge) conformation includes a central through portion 136 defined by a porous central portion 130 and lacks a porous outer wall 128.

Referring to FIG. 7(d), in one embodiment the thermoplastic composite body 102 having a trapezoidal block lacks a central through portion 136 and includes a porous outer wall 128 disposed along the first lateral surface 106 of the thermoplastic composite body 102, the second lateral surface 108 of the thermoplastic composite body 102, and the posterior surface 110 of the thermoplastic composite body, and further includes a dense edge 144 along the anterior surface 104 of the thermoplastic composite body 102.

Referring to FIG. 7(e), in one embodiment, wherein the at least one porous portion 122 forms the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 100, and the at least one dense portion 116 includes a plurality of dense cores 132, each of the plurality of dense cores 132 is disposed at vertices 150 between each of the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102.

Figure 8:
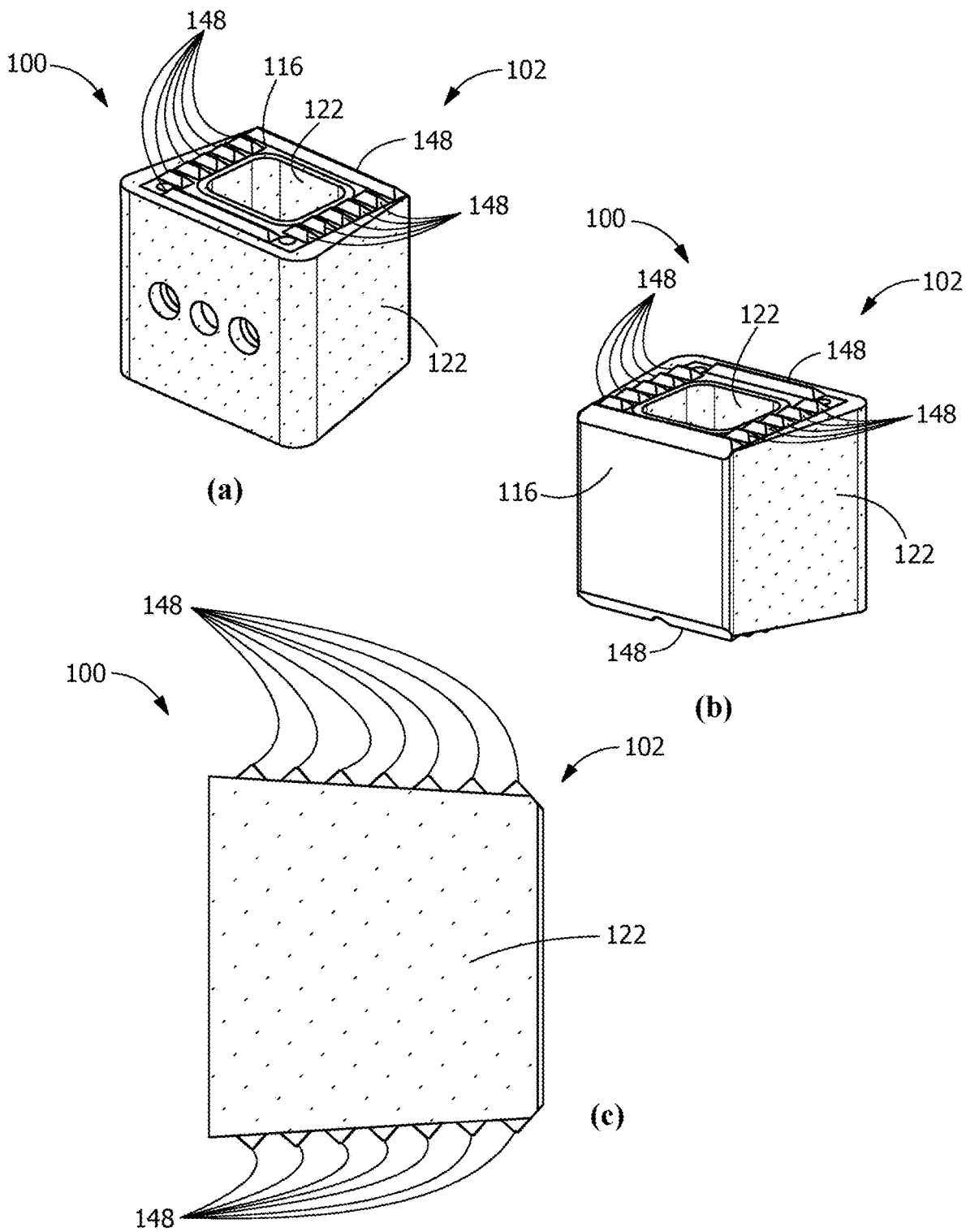
FIG. 8 shows an anterior perspective view (a), a posterior perspective view (b), and a lateral view (c) of an implantable medical device with a plurality of projections extending outward relative to the at least one porous portion from the superior and the inferior surface of the thermoplastic composite body, according to and embodiment of the disclosure.

Referring to FIG. 8, in one embodiment, the at least one dense portion 116 includes a plurality of projections 148 extending outward relative to the at least one porous portion 122 from at least one of the superior surface 112 of the thermoplastic composite body 102 or the inferior surface 114 of the thermoplastic composite body 102. Suitable projections 148 includes, but are not limited to, teeth, serrated teeth, ridges, bumps, and combinations thereof. Such projections 148 may come into direct contact with the adjacent peri-implant tissue to prevent movement relative to the peri-implant tissue after implantation. In another embodiment, the at least one dense portion 116 lacks any projections 148 extending outward relative to the at least one porous portion 122 from the superior surface 112 of the thermoplastic composite body 102 or the inferior surface 114 of the thermoplastic composite body 102.

Additionally, or alternatively, although not shown, the at least one dense portion 116 may include holes, notches, pins, radiographic markers, or other features that may be gripped or otherwise used for positioning of the implantable medical devices 100 comprising the at least one dense portion 116 by minimally invasive surgical tools and procedures.

Referring to FIGS. 2, 3, and 5-7, in one embodiment, the thermoplastic composite body 102 includes an insertion tool engagement feature 154. Suitable insertion tool engagement features 154 include, but are not limited to, a plurality of apertures 156 penetrating the anterior surface 104. In a further embodiment, at least one of the plurality of apertures 156 penetrates through a porous outer wall 128, a dense core 132, a porous central portion 130, and into a central through cavity 136, and at least one of the plurality of apertures 156 penetrates only into the porous outer wall 128. In yet a further embodiment, one of the plurality of apertures 156 penetrates through the porous outer wall 128, the dense core 132, the porous central portion 130, and into the central through cavity 136, and two of the plurality of apertures 156 penetrate only into the porous outer wall 128. The apertures 156 may, independently, be threaded or unthreaded.

Referring to FIGS. 1-8, vertices 150 between each of the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102 may be angular or radiused corners. Additionally, the superior surface 112 of the thermoplastic composite body 102 and the inferior surface 114 of the thermoplastic composite body 102 may, independently, meet the anterior surface 104 of the thermoplastic composite body 102, the first lateral surface 106 of the thermoplastic composite body 102, the second lateral surface 108 of the thermoplastic composite body 102, and the posterior surface 110 of the thermoplastic composite body 102, with angular, radiused, or chamfered corners. Further, in embodiments having at least one central through cavity 136, the superior surface 112 of the thermoplastic composite body 102 and the inferior surface 114 of the thermoplastic composite body 102 may, independently, meet the outer boundary 138 of the at least one central through cavity 136, with angular, radiused, or chamfered corners.

The first thermoplastic polymer matrix 118 and the second thermoplastic polymer matrix 126 may be formed from any suitable thermoplastic polymer materials, including, but not limited to, polyaryletherketone (PAEK), polyetheretherketone (PEEK), polyetherketonekteone (PEKK), polyetherketone (PEK), polyethylene, high density polyethylene (HDPE), ultra-high molecular weight polyethylene (UHMWPE), low density polyethylene (LDPE), polyethylene oxide (PEO), polyurethane, polypropylene, polypropylene oxide (PPO), polysulfone, polyethersulfone, polyphenyl sulfone, poly(DL-lactide) (PDLA), poly(L-lactide) (PLLA), poly(glycolide) (PGA), poly(ϵ-caprolactone) (PCL), poly (dioxanone) (PDO), poly(glyconate), poly(hydroxybutyrate) (PHB), poly(hydroxyvalerate (PHV), poly(orthoesters), poly(carboxylates), poly(propylene fumarate), poly(phosphates), poly(carbonates), poly(anhydrides), poly(iminocarbonates), poly(phosphazenes), polymethylmethacrylate (PMMA), polyacrylics from bisphenols, hydroxypropylmethacrylate (bis-GMA), tri(ethylene glycol) dimethacrylate (TEG-DMA), copolymers thereof, and blends thereof. The first thermoplastic polymer matrix 118 and the second thermoplastic polymer matrix 126 may be formed of the same thermoplastic polymer material or the first thermoplastic polymer matrix 118 may be distinct from the thermoplastic polymer material of the second thermoplastic polymer matrix 126.

The thermoplastic composite body 102 may include at least one reinforcement material dispersed throughout at least one of the at least one dense portion 116 and the at least one porous portion 122. Suitable bioactive reinforcement materials include, but are not limited to, hydroxyapatite (HA), calcium-deficient hydroxyapatite, carbonated calcium hydroxyapatite, beta-tricalcium phosphate (beta-TCP), alpha-tricalcium phosphate (alpha-TCP), amorphous calcium phosphate (ACP), anisometric calcium phosphate, octacalcium phosphate (OCP), tetracalcium phosphate, biphasic calcium phosphate (BCP), anhydrous dicalcium phosphate (DCPA), dicalcium phosphate dihydrate (DCPD), anhydrous monocalcium phosphate (MCPA), monocalcium phosphate monohydrate (MCPM), glasses and glass-ceramics comprising $SiO_2$, $CaO$, $Na_2O$, $Al_2O_3$, and/or $P_2O_5$, and combinations thereof. Suitable non-bioactive reinforcement materials include, but are not limited to, carbon fibers, carbon nanotubes, graphene, fiberglass, barium sulfate, metallic particles, oxide particle, and combinations thereof. The thermoplastic body 102 may include any suitable combination of bioactive reinforcement materials and non-bioactive reinforcement materials.

Reinforcement materials, for example, reinforcements in the form of calcium phosphate reinforcement particles, may be in the form of single crystals or dense polycrystals and in some embodiments may be, at least in some portion, anisometric. As used herein, "anisometric" refers to any particle morphology (shape) that is not equiaxed (e.g., spherical), such as whiskers, plates, fibers, etc. Anisometric particles are usually characterized by an aspect ratio. For example, HA single crystals are characterized by the ratio of dimensions in the c- and a-axes of the hexagonal crystal structure. Thus, the anisometric particles in the present disclosure have an aspect ratio greater than 1. In one example, the mean aspect ratio of the reinforcement particles is from greater than 1 to about 100. In accordance with the various embodiments, the mean aspect ranges from greater than 1, to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, and up to and including 100, including increments and ranges therein and there between.

The reinforcement particles can be provided in an amount of from about 1-60% by volume of the first thermoplastic polymer matrix 118 and/or the second thermoplastic polymer matrix 126, alternatively from about 20-50% by volume. In accordance with the various embodiments, the volume of reinforcement particles present in the first thermoplastic polymer matrix 118 and/or the second thermoplastic polymer matrix 126 can range from about 1-60%, alternatively from about 5-50%, alternatively from about 10-45%, alternatively from about 15-25%, and any suitable combination, sub-combination, range, or sub-range thereof by volume, based on the volume of the first thermoplastic polymer matrix 118 and/or the second thermoplastic polymer matrix 126. Thus, the reinforcement particles may be present, by volume, based on the total volume of the first thermoplastic polymer matrix 118 and/or the second thermoplastic polymer matrix 126, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 49, 50, 51, 52, 53, 54, 55, 56, 57, 58, 59, to about 60 volume percent, including increments and ranges therein and there between.

Furthermore, there are no limits on the size or amount of the reinforcement particles dispersed in the first thermoplastic polymer matrix 118 and/or the second thermoplastic polymer matrix 126, provided that the reinforcement particles are dispersed within and/or exposed at the surface in the first thermoplastic polymer matrix 118 and/or the second thermoplastic polymer matrix 126. For example, the reinforcement particles may have a maximum dimension from about 20 nm to about 2 mm, and for example, between and including 20 nm to about 100 μm. While both nano- and micro-scale reinforcement particles improve the mechanical properties of the first thermoplastic polymer matrix 118 and/or the second thermoplastic polymer matrix 126, nano-scale reinforcement particles are particularly effective for enhancing bioresorbability and cell attachment, and micro-scale particles are particularly effective for obtaining a uniform dispersion within the first thermoplastic polymer matrix 118 and/or the second thermoplastic polymer matrix 126. Amongst suitable reinforcement particles, calcium phosphate particles are effective for increasing bioactivity. Thus, the reinforcement particles may have a size from about 20 nm to about 20, 30, 40, 50, 60, 70, 80, 90, 100, 200, 300, 400, 500, 600, 700, 800, 900 nm, and to about 1 μm to about 10, 20, 30, 40, 50, 60, 70, 80, 90, 100, 200, 300, 400, 500, 600, 700, 800, 900 μm, and to about 1 mm and up to and including 2 mm, including increments and ranges therein and therebetween.

In one embodiment, the at least one porous portion 122 includes a second thermoplastic polymer matrix 126 reinforced with anisometric calcium phosphate particles. By way of example, a composite material may include a polyetheretherketone (PEEK) or a polyetherketoneketone (PEKK) matrix reinforced with various volume fractions of hydroxyapatite (HA) whiskers (e.g., 20 or 40 vol. %), wherein the second thermoplastic polymer matrix 126 is approximately between and including 50% and 95%, and in some embodiments between and including 60% and 85%, and in some particular embodiments between and including 65% and 75% porous.

In some such embodiments, the second thermoplastic polymer matrix 126 may also include bone morphogenetic protein (BMP) such as, for example, rhBMP-2, which can be absorbed, dispersed or accommodated by the void spaces and/or pores of the porous thermoplastic polymer scaffold 124 or microporous polymer matrix. Additionally, the BMP may be adsorbed to the calcium phosphate reinforcements further localizing the BMP to the surface of the porous thermoplastic polymer scaffold 124 or the second thermoplastic polymer matrix 126.

The porous thermoplastic polymer scaffold 124 may include a porous thermoplastic polymer (e.g., a PEEK polymer) scaffold having anisometric calcium phosphate reinforcement particles integrally formed or embedded with the porous thermoplastic scaffold and exposed on the surface of pores in the thermoplastic polymer scaffold 124. In this manner, the second thermoplastic polymer matrix 126 embedded with the reinforcement particles provides high material stiffness and strength, and the reinforcement particles exposed on the surface of the porous thermoplastic polymer scaffold 124 promote bioactivity and/or bioresorption. The reinforcement particles may further provide radiopacity (contrast for radiographic imaging). The porous thermoplastic polymer scaffold 124 includes a substantially continuous, interconnected porosity and a plurality of pores to promote bone ingrowth into the porous thermoplastic polymer scaffold 124. In addition, the porous thermoplastic polymer scaffold 124 is substantially continuously interconnected via a plurality of struts. Furthermore, at least one of the plurality of struts may be a load-bearing strut.

Additionally, the first thermoplastic polymer matrix 118 and the second thermoplastic polymer matrix 126 may optionally include other additives, if suitable. By way of non-limiting example, the first thermoplastic polymer matrix 118 and the second thermoplastic polymer matrix 126 may include one or more surface-active agents to enhance interfacial bonding between the reinforcement particles and thermoplastic polymer. The void spaces and/or pores may accommodate and deliver one or more growth factors such as, for example, BMP-2, to enhance osteoinductivity and/or bone regeneration. Furthermore, the void spaces and/or pores may also accommodate and deliver one or more transcription factors, matrix metalloproteinases, peptides, proteins, bone cells, progenitor cells, blood plasma, bone marrow aspirate, or combinations thereof, to improve speed bone regeneration, or resorption and replacement of the biomaterial. In some examples, the void spaces and/or pores may further accommodate a carrier material that may be incorporated into the void spaces and/or pores. The carrier material may include, for example, a collagen sponge, membrane, or a hydrogel material to deliver the growth factor material such as, for example, the BMP-2. The calcium phosphate reinforcements exposed on the surface of the porous thermoplastic scaffold, along with the porosity, improve the retention and localization of the BMP-2 within the porous thermoplastic scaffold and at the peri-implant interface.

In various embodiments, the porous thermoplastic polymer scaffold 124 may have pore sizes that range between and including 100 µm to about 1,000 µm, and, for example, from about 300 µm to about 500 µm. The thermoplastic polymer scaffold 124 may additionally contain some fraction of microporosity within scaffold struts that is less than about 10 µm in size. In accordance with the various embodiments, pores present in the thermoplastic polymer scaffold 124 can each have a size that ranges from about 10 µm to about 1,000 µm, including from about 10 µm to about 100 µm, from about 25 to about 85 µm, from about 40 µm to about 65 µm, and from about 100 µm to about 500 µm, from about 150 µm to about 450 µm, from about 200 µm to about 400 µm, from about 250 µm to about 350 µm, and any suitable combination, sub-combination, range, or sub-range thereof. The thermoplastic polymer scaffold 124 may include pores having sizes that are different, wherein at least a portion of the pores has a different size than other pores, each pore having a different size within the range from about from about 10 µm to about 1000 µm. Thus, the pores may have a size from about 1, 10, 20, 30, 40, 50, 60, 70, 80, 90, 100, 125, 150, 175, 200, 225, 250, 275, 300, 325, 350, 375, 400, 425, 450, 475, 500, and up to and including 1,000 µm, including increments and ranges therein and there between.

In various embodiments, the at least one porous portion 122 may include an amount of porosity up to 95%, including from 50% to about 90% by volume, and, for example, between and including about 70% to 90% by volume. In accordance with the various embodiments, the extent of porosity in the at least one porous portion 122 may range from 50% to about 95%, from about 55% to about 90%, from about 60 to about 85%, from about 65 to about 80% from about 65 to about 75%, from about 70 to about 75%, and any suitable combination, sub-combination, range, or sub-range thereof by volume, based on the volume of the at least one porous portion 122. Thus, the extent of pores, by volume, based on the total volume of the at least one porous portion 122, can be from 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 to about 95 volume percent, including increments and ranges therein and therebetween.

In one embodiment, the thermoplastic composite body 102 includes a ratio of cross-sectional area of the at least one porous portion 122 to the at least one dense portion 116 normal to loading that provides an overall stiffness for the thermoplastic composite body within 20% of adjacent vertebral bodies between which the implantable medical device 100 is inserted. This ratio may be tailored with respect to the adjacent vertebral body composition, such as, by way of example, cancellous bone tissue or cortical bone tissue. In one embodiment, the at least one porous portion 122 includes an elastic modulus within 20% of cancellous bone, and the at least one dense portion 116 includes an elastic modulus within 20% of cortical bone. In one embodiment overall stiffness in axial (superior-inferior) compression is within 20% of that for adjacent cervical, thoracic and/or lumbar vertebral bodies which are known to exhibit a stiffness in axial compression in the range of about 0.5 to about 40 kN/mm, and more commonly from about 1 to about 6 kN/mm. The at least one dense portion 116 may include an elastic modulus within 20% of that for cortical bone which is known to exhibit an elastic modulus in the range of about 5 to about 25 GPa. The at least one porous portion 122 may include a compressive elastic modulus within 20% of that for cancellous bone, which is known to exhibit a compressive elastic modulus in the range of about 20 to about 1,000 MPa.

The implantable medical device according to claim 1, wherein the thermoplastic composite body includes a stiffness in axial (superior-inferior) compression less than about 20 kN/mm and a block stiffness in axial compression greater than about 800 N/mm. As used herein, "block stiffness" is a measure of how readily an implant subsides into adjacent bone superior and inferior to the implant upon loading in axial compression, as set forth in ASTM F2267. As known by one skilled in the art, a higher block stiffness indicates a greater resistance to subsidence, whereas a lower block stiffness indicates a lesser resistance to subsidence.

The thermoplastic composite body 102 may be manufactured by methods common to reinforced thermoplastic and thermosetting polymers, including but not limited to injection molding, reaction injection molding, compression molding, transfer molding, extrusion, blow molding, pultrusion, casting/potting, solvent casting, microsphere sintering, fiber weaving, solvent casting, electrospinning, freeze drying (lyophilization), thermally induced phase separation, gas foaming, and rapid prototyping processes such as solid freeform fabrication, robotic deposition (aka, robocasting), selective laser sintering, fused deposition modeling, three-dimensional printing, laminated object manufacturing, stereolithography, or any other suitable processes or combinations thereof.

Figure 9:
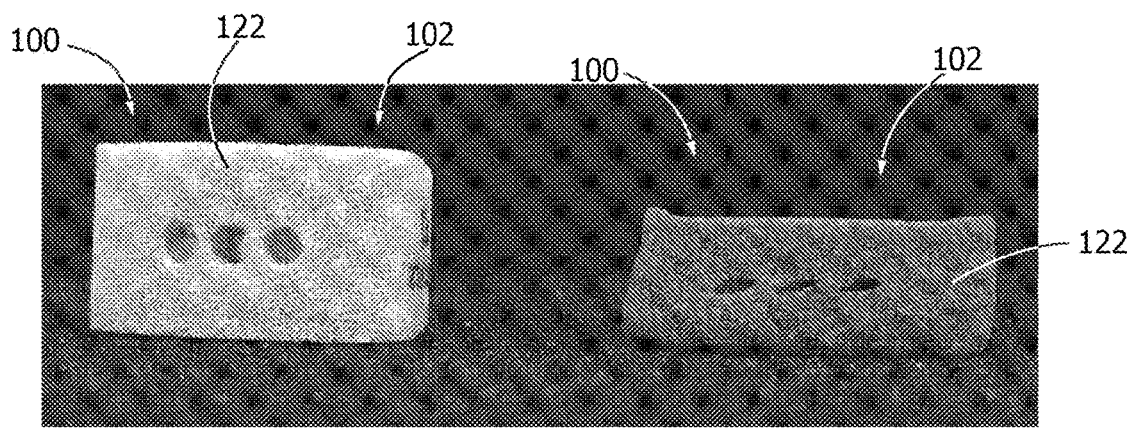
FIG. 9 shows a photograph comparing implantable medical devices before and after being subjected to an overload in axial compression, which caused deformation rather than fracture, according to and embodiment of the disclosure.

Referring to FIG. 9, in one embodiment the thermoplastic composite body 102 is non-destructively compressible in the direction of loading by at least about 10% of the thickness dimension 120, alternatively by at least about 15%, alternatively by at least about 20%, alternatively by at least about 25%, alternatively by at least about 30%, alternatively by at least about 35%, alternatively by at least about 40%, alternatively by at least about 45%, alternatively by at least about 50%. As used herein, "non-destructively compressible" indicates elastic or non-elastic compression without fracture of the thermoplastic composite body 102.

Figure 10:
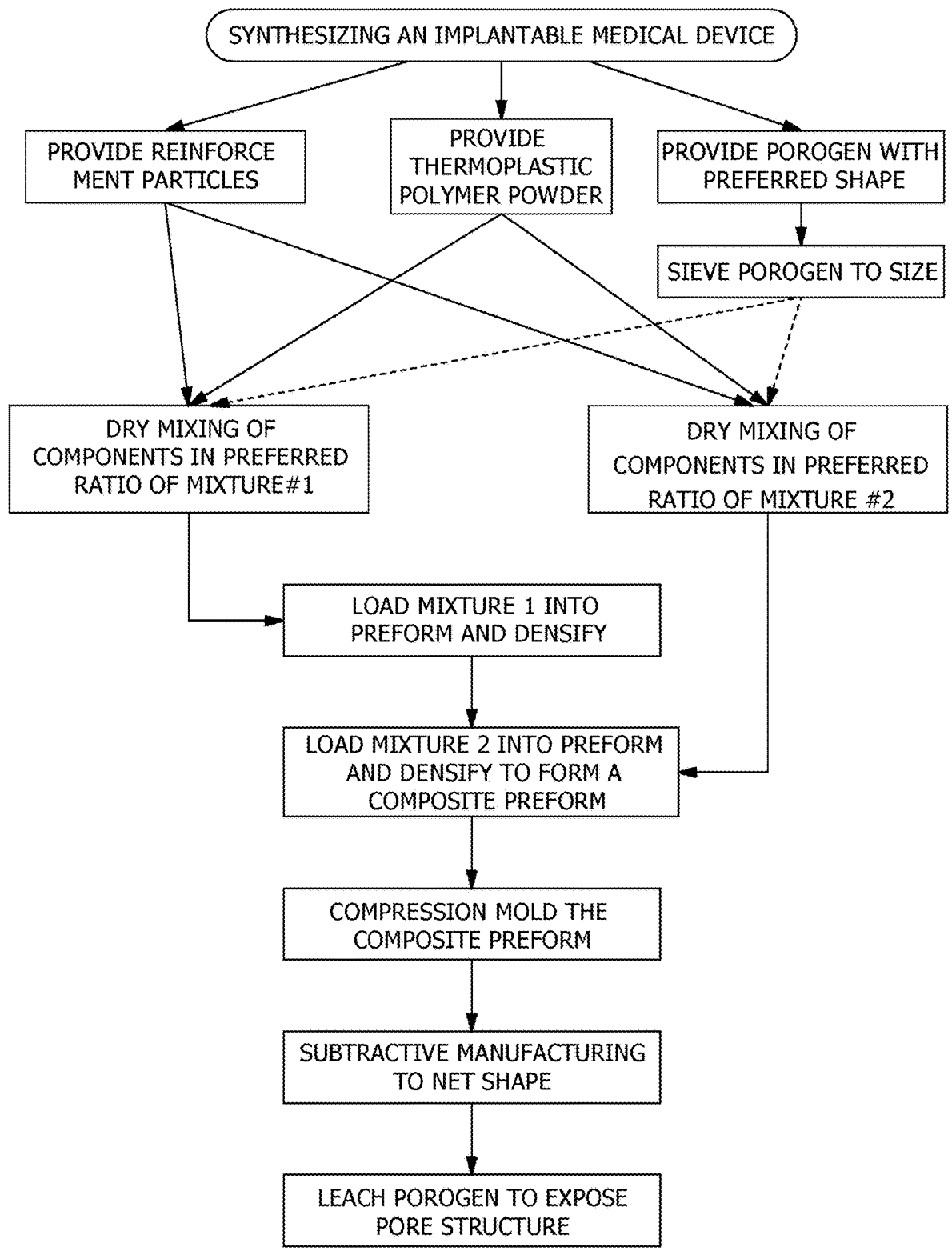
FIG. 10 shows a flow chart of a representative method of forming an implantable medical device by dry mixing the provided powders, according to an embodiment of the disclosure.

Referring to FIG. 10, in one embodiment, a method that may be used to prepare a thermoplastic composite body 102 is provided. While an exemplary manner of synthesizing the thermoplastic composite body 102 has been illustrated in FIG. 10, one or more of the steps and/or processes illustrated in FIG. 10 may be combined, divided, re-arranged, omitted, eliminated and/or implemented in any other way. Further still, the exemplary method of FIG. 10 may include one, or more processes and/or steps in addition to, or instead of, those illustrated in FIG. 10, and/or may include more than one of any or all of the illustrated processes and/or steps. Further, although the exemplary method is described with reference to the flow chart illustrated in FIG. 10, persons of ordinary skill in the art will readily appreciate that many other methods of synthesizing the example composite material may alternatively be used.

Figure 11:
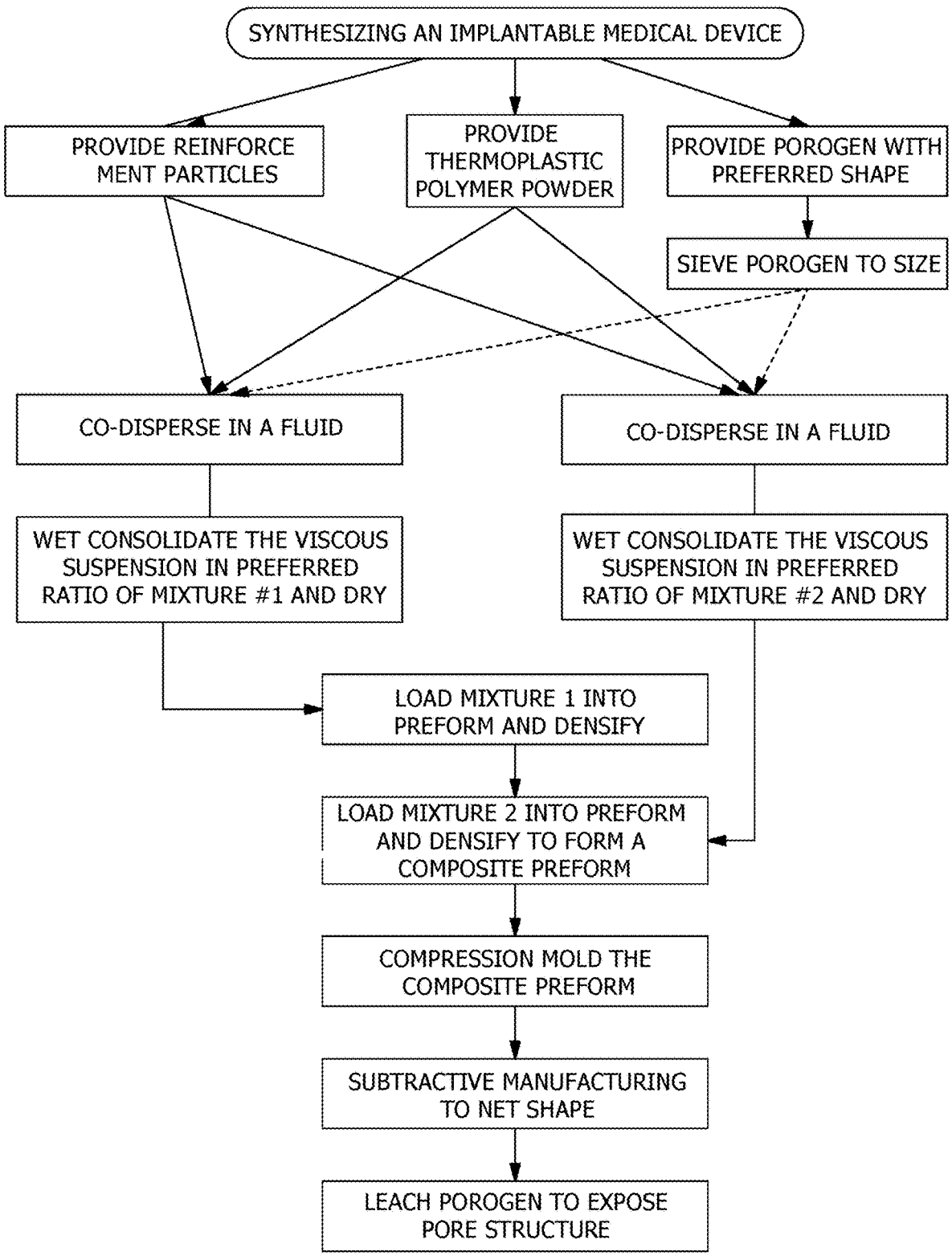
FIG. 11 shows a flow chart of a representative method of forming an implantable medical device by wet solution mixing the provided powders, according to an embodiment of the disclosure.

Referring to FIG. 11, the thermoplastic composite body 102 may be processed using a powder processing approach in conjunction with compression molding and particle leaching techniques and is particularly suited for achieving a relatively high concentration (e.g., >20 vol %) of well-dispersed (and aligned, if desired) anisometric calcium phosphate reinforcements (e.g., HA whiskers) in a thermoplastic matrix (e.g., PEEK) with minimal degradation of the calcium phosphate size/shape during processing. In this manner, the calcium phosphate reinforcement volume fraction, aspect ratio, size and orientation; the polymer; and the size, volume fraction, shape and directionality of the void space and/or porosity may be tailored to vary the mechanical properties of the composite material.

A polymer such as, for example, PEEK, and reinforcements, such as HA whiskers, are provided in powder form. The PEEK polymer powder may have, for example, a mean particle size of about 10 μm. The HA whiskers may be synthesized using, for example, molten salt synthesis, hydrothermal synthesis, the chelate decomposition method, precipitation, solvothermal synthesis, precursor pyrolysis, solid state reactions, and the like.

The polymer powder, for example, a PAEK polymer powder such as PEEK, and reinforcement, such as, for example, synthesized HA whiskers, optionally together with a porogen, as further described herein below, are co-dispersed, either in a fluid such as, for example ethanol, and mixed using, for example, ultrasonication under constant stirring—forming a viscous suspension, or as a dry mixture using powder blending methods known to the industry. The amount of each component may be varied to obtain the desired mixture by the percentage of HA relative to the polymer powder and the percentage of HA and polymer blend relative to the porogen. Of course, depending on the polymer selected, where for example the polymer is not a PAEK polymer, other forms of mixing may be employed for inclusion of a porogen, such as for example, solvent mixing.

In one example, after the polymer powder and the reinforcement are mixed, the porosity of the composite material is selectively varied and/or tailored by any one of a variety of methods, for example as described below.

In one such example, the porosity may be formed and tailored by the addition of a suitable porogen material such as, for example, NaCl, wax, polysaccharides (sugars), cellulose, polymer or glass beads, and the like. The extent of the porosity can be controlled by varying the amount of porogen used, and the pore size could be tailored by sieving the porogen to a desired size prior to mixing the porogen with the polymer mixture, or by selecting a porogen having a specified controlled size, or by blending one or more porogens of different sizes, or combinations of these. In various examples, one or more porogen employed for the formation of pores may have a size that ranges from between and including 100 μm to about 1,000 μm, and, for example, from about 300 μm to about 500 μm. It is contemplated that while the ranges contemplate average porogen size, there may be some porogen particles that are larger or smaller than the average, and thus, there may be porogen particles that have a size below 100 μm, and thus some porogen particles may have a size in the range from 10 μm to 100 μm. Likewise, there may be particles that have a size that is greater than 1,000 μm. In accordance with the various embodiments, porogens employed for forming pores in the composite material can have a size that ranges from about 10 μm to about 1,000 μm or greater than 1,000 μm, including from about 10 μm to about 100 μm, from about 25 to about 85 μm, from about 40 μm to about 65 μm, and from about 100 μm to about 500 μm, from about 150 μm to about 450 μm, from about 200 μm to about 400 μm, from about 250 μm to about 350 μm, and any suitable combination, sub-combination, range, or sub-range thereof. The disclosure contemplates the use of one or more porogen that includes sizes that are different, wherein the porogen comprises a blend of sizes within the range from about from about 10 μm to about 1000 μm. Thus, the any one or more porogen may have a size from about 1, 10, 20, 30, 40, 50, 60, 70, 80, 90, 100, 125, 150, 175, 200, 225, 250, 275, 300, 325, 350, 375, 400, 425, 450, 475, 500, and up to and including 1,000 μm, including increments and ranges therein and there between.

In various examples, one or more porogen employed for the formation of pores may have any shape, which may be irregular or regular, for example, but not limited to, spheres, cubes, fibers, polyhedra, and the like. Indeed, a plurality of porogens may be used each having a different shape. In some particular examples, a porogen is select that has generally rounded surfaces.

In another such example, the porosity and/or the pore size of the polymer matrix may be selectively varied using any other suitable methods and/or process(es) such as, for example, microsphere sintering, fiber weaving, solvent casting, electrospinning, freeze drying (lyophilization), thermally induced phase separation, gas foaming, and rapid prototyping processes such as solid freeform fabrication, robotic deposition (aka, robocasting), selective laser sintering, fused deposition modeling, three-dimensional printing, laminated object manufacturing, stereolithography, etc., or any other suitable process(es) or combination(s) thereof. The viscous suspension may be wet-consolidated by, for example, vacuum filtration, and drying to remove any residual fluid (i.e., ethanol or other solvents). In other embodiments that do not include fluid, the powder components may be arranged such that the material to be porous (the dry mixture containing the porogen) are in the regions of a preform which is desired to be porous; and the regions that are to be more dense, are filled with the dry mixture that has less porogen in it. The composite mixture is densified by, for example, uniaxial compression, to form a composite preform. In one embodiment each region of material is densified before the next region of a different density is added. At completion, each region will be densified with the relatively equal compression.

Following the initial densification, the preform is compression molded and/or sintered at elevated temperatures (e.g., approximately 20° C. to 400° C.) sufficient to fuse the polymer particles with minimal damage to the reinforcement particles. The process or composite material may be heated to a desired processing temperature and the implant may be shaped or formed. Densifying and molding the composite material may include aligning the reinforcement particles (e.g., HA whiskers) morphologically and/or crystallographically within the scaffold struts. Thus, in accordance with the various embodiments, the temperature for molding is in the range (° C.) from and including 20 to about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 to 400° C. including increments and ranges therein and there between.

The porous thermoplastic polymer scaffold 124 may have any shape and/or size (e.g., any polygonal shape), and may be formed by methods common to reinforced thermoplastic and thermosetting polymers, including but not limited to injection molding, reaction injection molding, compression molding, transfer molding, extrusion, blow molding, pultrusion, casting/potting, solvent casting, and rapid prototyping processes such as solid freeform fabrication, robotic deposition (also known as robocasting), selective laser sintering, fused deposition modeling, three-dimensional printing, laminated object manufacturing, stereolithography, etc., or any other suitable processes. The thermoplastic composite body 102 may be formed by the mold walls and/or machining after molding. The porous thermoplastic polymer scaffold 124 undergoes a leaching process to remove, for example, the porogen used during synthesis of the porous thermoplastic polymer scaffold 124. The leaching may occur, for example, via a dissolution method, heating method, and/or any other suitable methods and/or process (es). More specifically, dissolution may include immersing the porous thermoplastic polymer scaffold 124 in a fluid, such as, for example, deionized water. Furthermore, viscous flow of the polymer/reinforcement mixture during molding can be designed to tailor the preferred orientation of the anisometric reinforcements in the implant. Additionally, surface-active agents may be added during the mixing process and/or to the surface of the porous thermoplastic polymer scaffold 124 to enhance interfacial bonding between reinforcement particles and the second thermoplastic polymer matrix 126.

Figure 12:
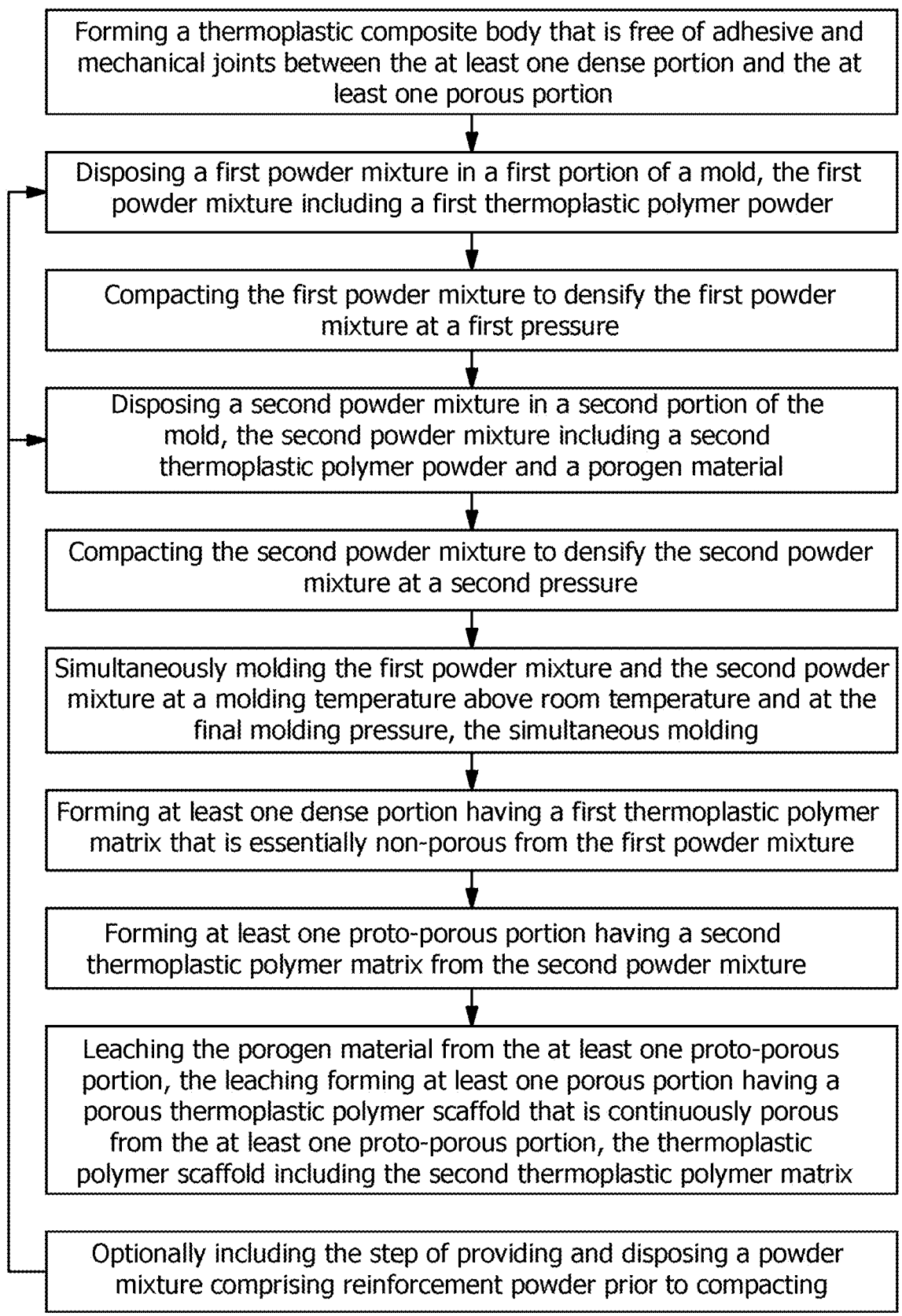
FIG. 12 shows a flow chart of a representative method of forming an implantable medical device by dry mixing the provided powders, according to an embodiment of the disclosure.

Referring to FIG. 12, in one embodiment, a method for forming a thermoplastic composite body 102 includes disposing a first powder mixture in a first portion of a mold, the first powder mixture including a first thermoplastic polymer powder. The first powder mixture is compacted to densify the first powder mixture at a first pressure. A second powder mixture is disposed in a second portion of the mold, the second powder mixture including a second thermoplastic polymer powder and a porogen material. The second powder mixture is compacted to densify the second powder mixture at a second pressure. The first powder mixture and the second powder mixture are simultaneously molded at a molding temperature above room temperature and at a final molding pressure. The simultaneous molding forms at least one dense portion 116 having a first thermoplastic polymer matrix 126 that is essentially non-porous from the first powder mixture and at least one proto-porous portion having a second thermoplastic polymer matrix 126 from the second powder mixture. The porogen material is leached from the at least one proto-porous portion, forming at least one porous portion 122 having a porous thermoplastic polymer scaffold 124 that is continuous from the at least one proto-porous portion. The thermoplastic polymer scaffold 124 includes the second thermoplastic polymer matrix 126. The simultaneous molding and the leaching integrally form the at least one dense portion 116 and the at least one porous portion 122 as a single continuous article free of adhesive and mechanical joints between the at least one dense portion 116 and the at least one porous portion 122. In a further embodiment, either or both of the first powder mixture and the second powder mixture may include reinforcement particles.

In one embodiment, the first powder mixture and the second powder mixture are compacted below the molding temperature. In a further embodiment, the first powder mixture and the second powder mixture are compacted at room temperature. The molding temperature may be any suitable temperature, including, but not limited to between 100° C. to about 450° C., alternatively between 100° C. to about 200° C., alternatively between 150° C. to about 250° C., alternatively between 200° C. to about 300° C., alternatively between 250° C. to about 350° C., alternatively between 300° C. to about 400° C., alternatively between 350° C. to about 450° C. Of course, it will be appreciated by one of ordinary skill that thermoplastic polymers will be molded at a temperature above the glass transition temperature and below the thermal decomposition temperature.

In one embodiment, following simultaneously molding the first powder mixture and the second powder mixture, subtractive manufacturing (i.e., material removal) is utilized to form the net shape of the thermoplastic composite body 102 prior to leaching the porogen material from the at least one proto-porous portion.

The first pressure may be below, at, or above, the final molding pressure. The second pressure may be below, at, or above, the final molding pressure. The second pressure may be lower, the same as, or higher than the first pressure. The final molding pressure may be any suitable pressure, including, but not limited to, at least 3 MPa, or alternatively at least 5 MPa, or at least 10 MPa, or at least 15 MPa, or at least 20 MPa, or at least 25 MPa, or at least 30 MPa, or at least 35 MPa, or at least 40 MPa, alternative at least 45 MPa, or at least 50 MPa, or at least 55 MPa, or at least 60 MPa, or at least 65 MPa, or at least 70 MPa, or at least 75 MPa, or at least 80 MPa, or at least 85 MPa, or at least 90 MPa, or at least 95 MPa, or at least 100 MPa, or at least 150 MPa, or at least 200 MPa, or at least 250 MPa.

EXAMPLES

Figure 13:
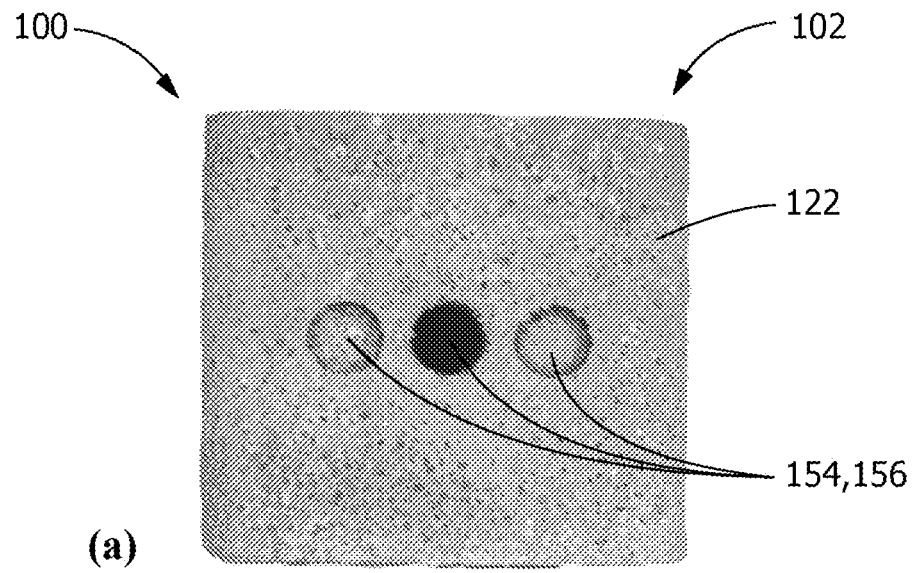
FIG. 13 shows anterior (a), lateral (b), and superior (c) photographs of an exemplary implantable medical device, according to an embodiment of the disclosure.
Figure 13:
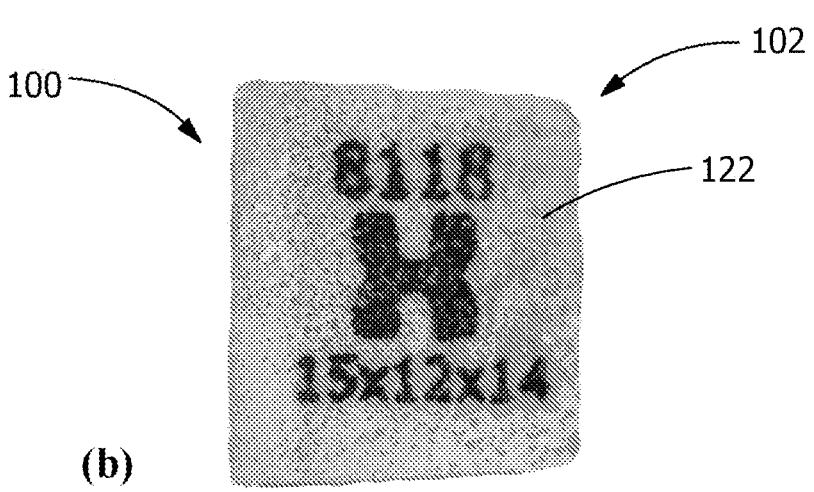
Figure 13:
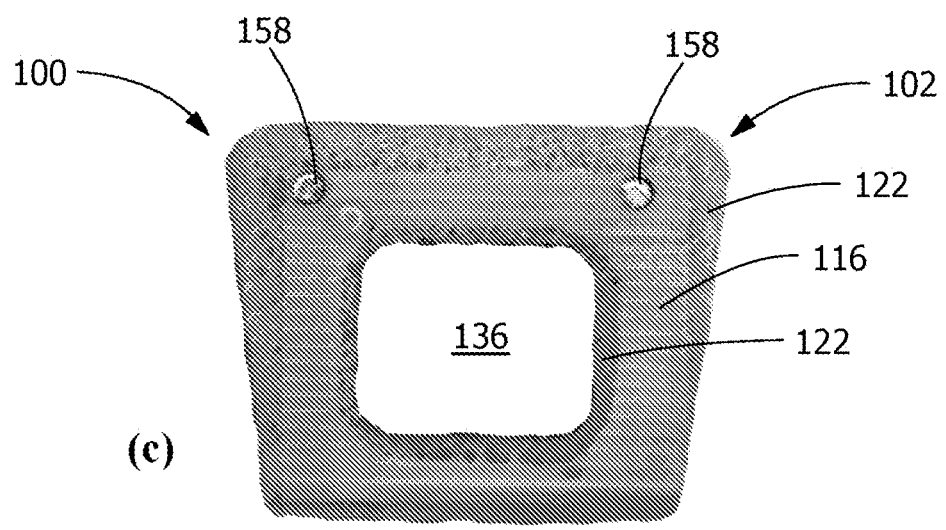

Referring to FIG. 13, an exemplary cervical interbody fusion cage was prepared following the specifications and methods disclosed herein with overall dimensions measuring 15 by 12 by 14 mm. This thermoplastic composite body 102 includes a porous outer wall 128 disposed along the anterior surface 104 of the thermoplastic composite body 102, the first lateral surface 106 of the thermoplastic composite body 102, and the second lateral surface 108 of the thermoplastic composite body 102, and the dense core 132 is disposed between the at least one porous central portion 130 and the porous outer wall 128, and extends to the posterior surface 110 of the thermoplastic composite body 102 forming a dense posterior edge 134. The porous central portion 130 is 0.5 mm thick and defines the outer boundary 138 of the central through cavity 136. The central through cavity 136 contains 0.21 mL of volume. The dense core 132 is 1.5 to 2 mm thick at all points along the closed structural support 152. The superior surface 112 area of the at least one porous portion 122 is about 45 mm$^2$, and the superior surface 112 area of the at least one dense portion 116 is about 77 mm$^2$, indicating a cross-sectional surface ratio of at least one porous portion 122 to the at least one dense portion 116 normal to loading of about 0.6. The first thermoplastic polymer matrix 118 and the second thermoplastic polymer matrix 126 is comprised of polyetheretherketone (PEEK) with 20 vol. % hydroxyapatite whisker reinforcements. The at least one porous portion 122 includes about 70-75 vol. % porosity, and the pores thereof are about 200-500 µm in size. Hydroxyapatite whiskers are both embedded within the first thermoplastic polymer matrix 118 and the second thermoplastic polymer matrix 126 and are also exposed on scaffold struts surfaces within pore spaces of the porous thermoplastic polymer scaffold 124.

Exemplary implantable medical devices 100 were prepared in accordance with FIG. 13 a PEEK powder, about 10 µm in size, hydroxyapatite whisker reinforcements, about 5 µm in diameter and with a length-to-diameter aspect ratio ranging from about 3 to about 10, and a spherical sodium chloride porogen, about 250-400 µm in diameter. A first powder mixture, including a PEEK powder, HA whisker reinforcements, and sodium chloride porogen, was dispensed into a mold in locations corresponding proto-porous regions of the implant, wherein for the medical device 100 described herein above, this corresponds to the proto-porous regions of the outer porous wall. The first powder mixture was compacted by uniaxial compression at a pressure of 125 MPa at ambient temperature into a specific region of a cylindrical mold. A second powder mixture, including a PEEK powder and HA whisker reinforcements, was then dispensed into the same mold in specific regions corresponding to the location of dense regions of the implant. The second powder mixture was compacted by uniaxial compression at a pressure of 250 MPa at ambient temperature. A third dispensing was performed, filling the remainder of proto-porous regions of the implant, wherein for the medical device 100 described herein above, this corresponds to the proto-porous regions of the porous central portion, using the first powder mixture with porogen, polymer and HA whisker reinforcements, and compacted by itself to 125 MPa. Each entire exemplary implantable medical device 100, including both porous portions 122 and dense portions 116 simultaneously, was then compression molded at a temperature of 375° C. and a pressure of 250 MPa. After molding, the consolidated round billet was cooled and ejected from the mold. Exterior implant surfaces and a central cavity were created by material removal using a high-speed end mill. Holes were drilled into the dense material region to accommodate the insertion of tantalum pins 158 serving as radiographic markers. The exemplary implantable medical devices 100 were then cleaned in Alconox™ to remove any contamination from the machining process. The porogen was subsequently removed by soaking the exemplary implantable medical devices 100 in deionized water for 5 hours at 50° C., under ultrasonication and vacuum. The exemplary implantable medical devices 100 were dried in a drying oven at 40° C.

The exemplary implantable medical devices 100 were tested according to the methods outlined in ASTM F2077 and F2267, which are well-known in the art. An exemplary implantable medical device 100 tested in static axial compression exhibited a stiffness of 18.4 kN/mm, a yield force of 10.3 kN, and an ultimate force of 11.4 kN. An exemplary implantable medical device 100 tested in static compressive shear exhibited a stiffness of 3.3 kN/mm, a yield force of 5.1 kN and an ultimate force of 5.2 kN. An exemplary implantable medical device 100 tested in dynamic axial compression in phosphate buffered saline at 37° C. at 5 Hz with a maximum applied force of 1,500 N and minimum applied force of 150 N, exhibited runout at 5 million cycles. An exemplary implantable medical device 100 tested in static axial compression in between two polyurethane foam test blocks, which mimic adjacent cancellous bone, exhibited a test block stiffness (Kp) of 1,068 N/mm.

Figure 14:
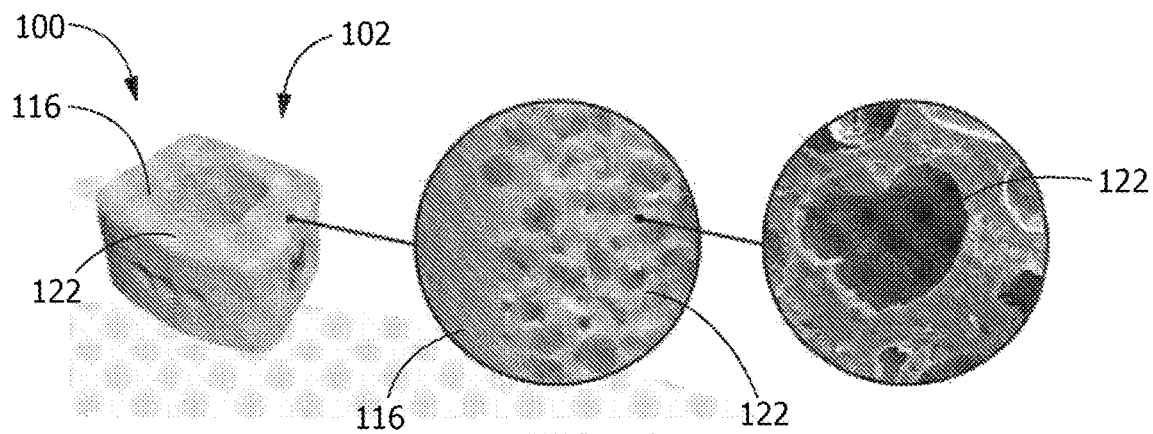
FIG. 14 shows photographs presenting expanded views of the porous structure of implantable medical devices, according to an embodiment of the disclosure.
Figure 15:
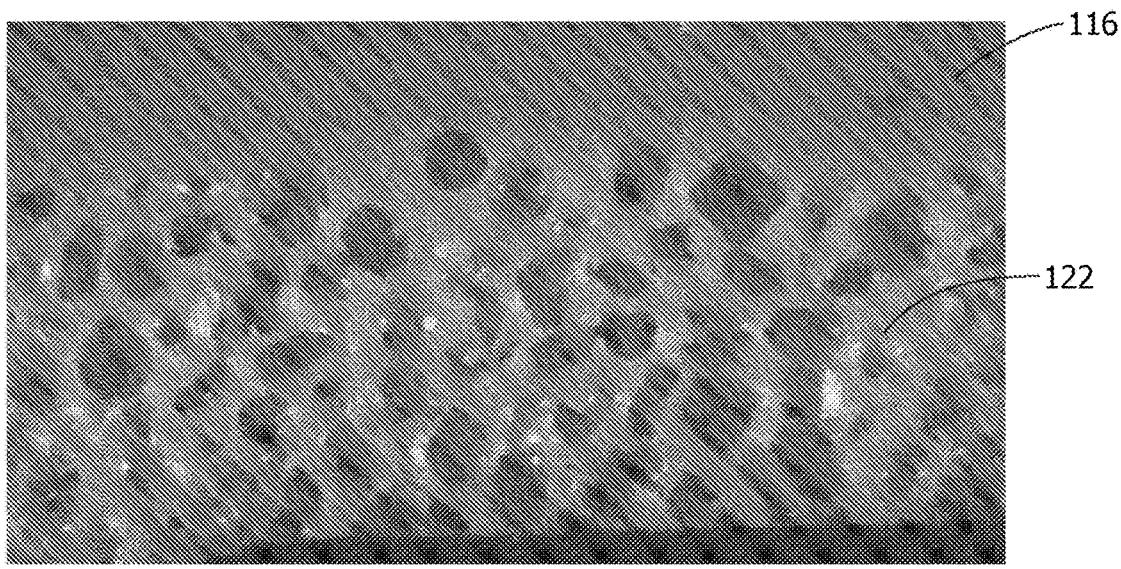
FIG. 15 shows a photograph presenting an expanded view of the thermoplastic polymer matrix that is continuous between a porous portion and a dense portion of an implantable medical device, according to an embodiment of the disclosure.
Figure 16:
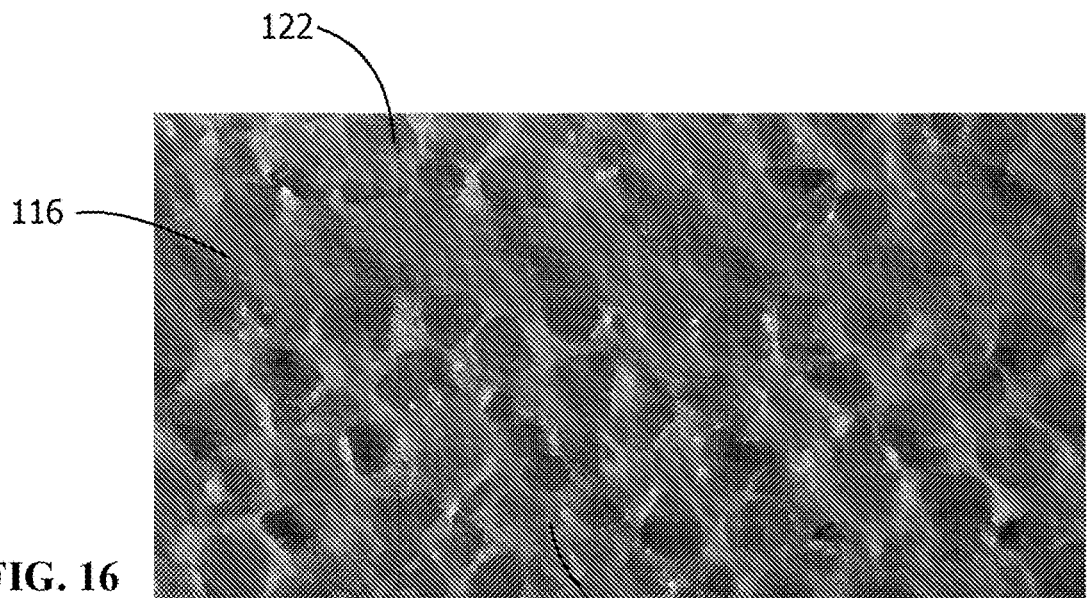
FIG. 16 shows a photograph presenting an expanded view of the thermoplastic polymer matrix that is continuous between a porous portion and a dense portion of an implantable medical device, according to an embodiment of the disclosure.

Referring to FIGS. 14-16, exemplary implantable medical devices 100 show that the thermoplastic composite body 102 is integrally formed as a single continuous article free of adhesive and mechanical joints between the at least one dense portion 116 and the at least one porous portion 122. The interface between the at least one porous portion 122 and the at least one dense portion 116, as shown in FIGS. 14-16 is free of any discernible mechanical or adhesive joint. Thus, as exemplified in the drawings, the thermoplastic polymer matrix is continuous between a porous portion and a dense portion of an implantable medical device, according to an embodiment of the disclosure.

Figure 17:
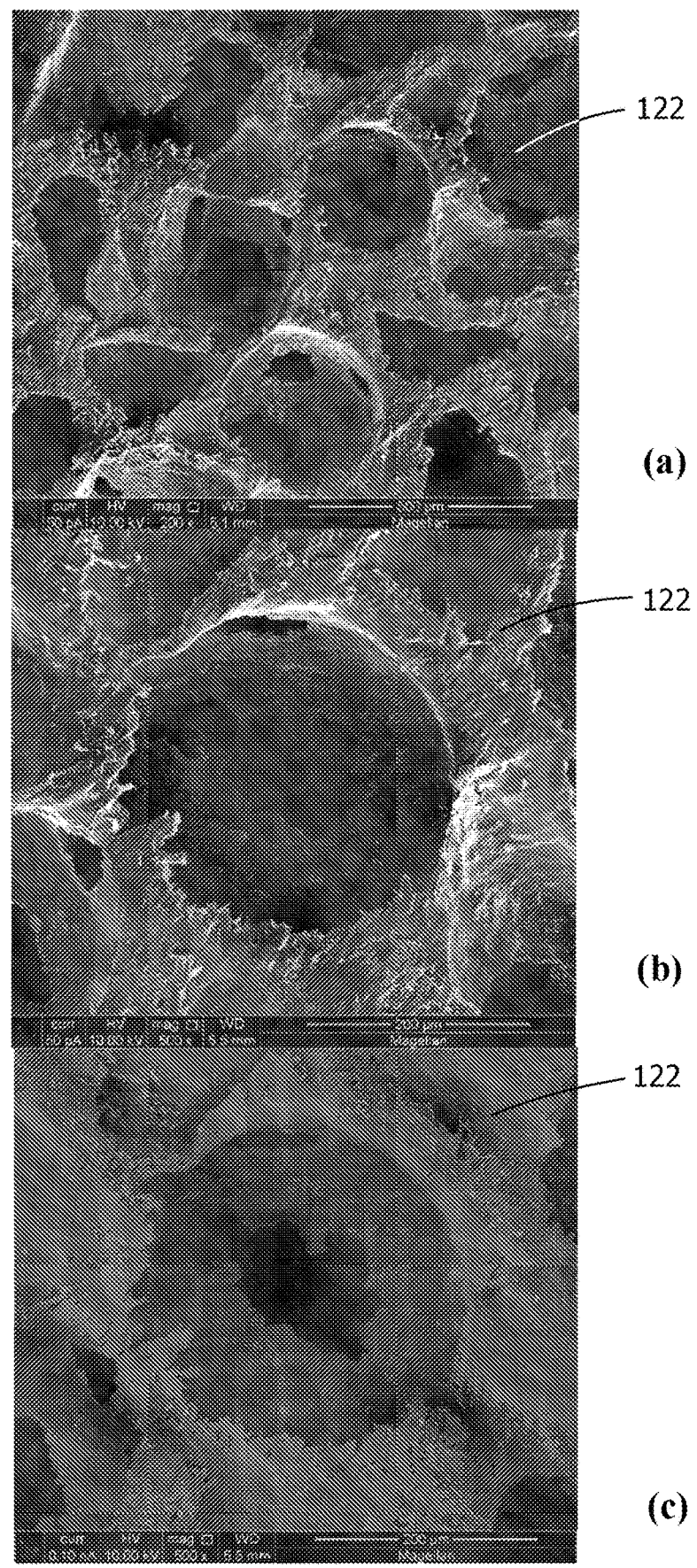
FIG. 17 shows scanning electron micrographs of a porous portion at (a) a lower magnification, (b) a higher magnification, and (c) the higher magnification with backscattered electron imaging, according to an embodiment of the disclosure.

Referring to FIG. 17, scanning electron micrographs are shown of a porous portion 122 of an implantable medical device 100 at a lower magnification (a), a higher magnification (b), and at the higher magnification with backscattered electron imaging, according to an embodiment of the disclosure.

Figure 18:
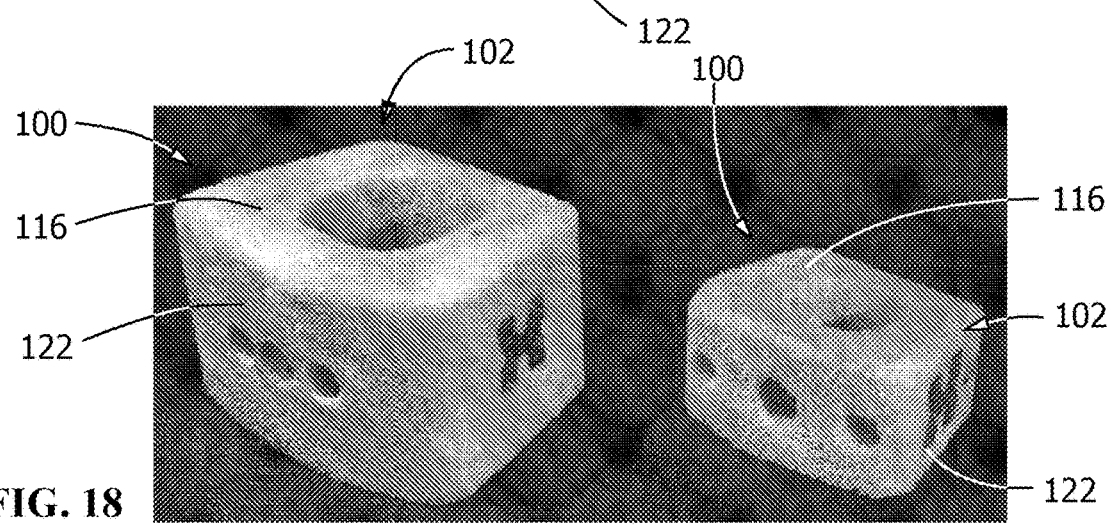
FIG. 18 shows a photograph with two implantable medical devices having different ratios of the cross-sectional area of the porous and dense regions, according to and embodiment of the disclosure.

Referring to FIG. 18, two implantable medical devices 100 prepared by the methods described herein are shown in a photograph, each implantable medical device 100 having different ratios of the cross-sectional area of the porous 122 and dense 116 portions.

Figure 19:
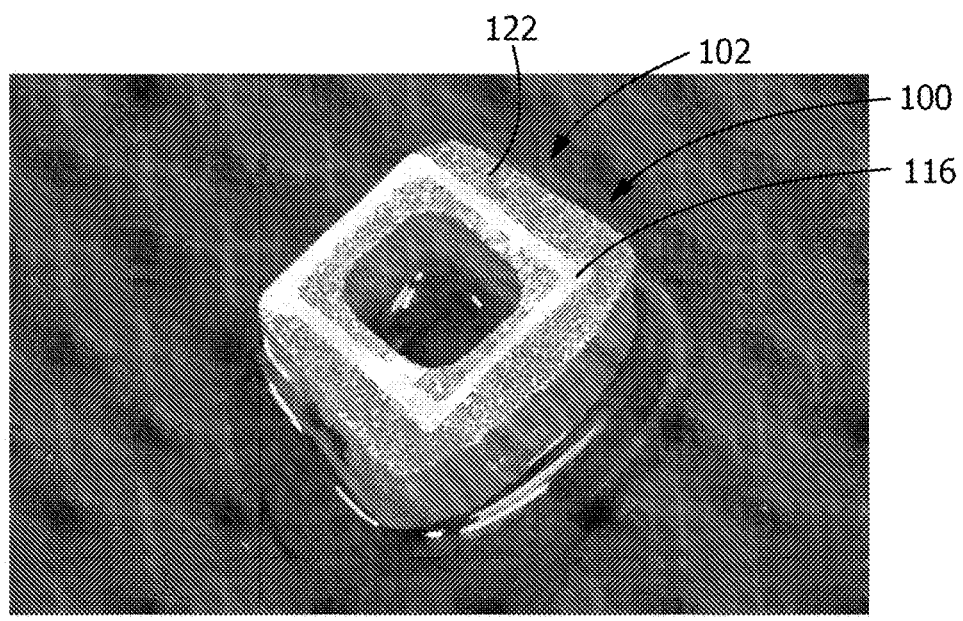
FIG. 19 shows a photograph of an implantable medical device resting in colored aqueous solution, with the aqueous solution being drawn into the porous portion by capillary action and hydrophilicity, emphasizing the distinction between the porous and dense portions, according to an embodiment of the disclosure.

Referring to FIG. 19 a photograph of an exemplary implantable medical device 100 shows the implantable medical device 100 resting in colored aqueous solution, with the aqueous solution being drawn into the porous portion by capillary action and hydrophilicity, emphasizing the distinction between the porous 122 and dense 116 portions, and provides a high-contrast view of the clear transitions between the at least one porous portion 122 and the at least one dense portion 116.

The exemplified embodiments of implantable medical devices 100 described herein are representative of implantable medical devices 100 that include polymeric materials, for example, PAEK materials, that may include one or more of reinforcement particles and porosity. It will be appreciated that these materials may be used in accordance with the teachings herein for other bony implant applications, such as for implant fixation, fraction fixation, synthetic bone graft substitutes, interbody spinal fusion, tissue engineering scaffolds, and other applications, and the implants may be tailored to provide specific mechanical, biological, and surgical functions by varying the distribution and proportions of dense and porous polymer, and by varying one or more of the polymer composition and molecular orientation, porosity and pore size of the porous thermoplastic scaffold, or the reinforcement, for example, HA, content, morphology, preferred orientation, and size.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated.

As used herein, the singular forms "a," "an," and "the" are intended to include the plural forms as well, unless the context clearly indicates otherwise. Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention.

All ranges and amounts given herein are intended to include subranges and amounts using any disclosed point as an end point. Similarly, a range given of "about 1 to 10 percent" is intended to have the term "about" modifying both the 1 and the 10 percent endpoints, and meaning within 10 percent of the indicated number (e.g. "about 10 percent" means 9-11 percent and "about 2 percent" means 1.8-2.2 percent). Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements. Thus, while exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The above description is only illustrative of the preferred embodiments which achieve the objects, features and advantages of the present invention. It is not intended that the present invention be limited to the illustrated embodiments. While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An implantable medical device, comprising:
   a thermoplastic composite body including:
      an anterior surface of the thermoplastic composite body;
      a first lateral surface of the thermoplastic composite body;
      a second lateral surface of the thermoplastic composite body;
      a posterior surface of the thermoplastic composite body;
      a superior surface of the thermoplastic composite body;
      an inferior surface of the thermoplastic composite body;
      at least one dense portion formed of a first thermoplastic polymer matrix that is essentially non-porous; and
      at least one porous portion formed of a porous thermoplastic polymer scaffold, the porous thermoplastic polymer scaffold being formed of a second thermoplastic polymer matrix,
      wherein the at least one dense portion and the at least one porous portion are integrally formed such that the thermoplastic composite body is a single continuous article free of adhesive joints between the at least one dense portion and the at least one porous portion and free of mechanical joints between the at least one dense portion and the at least one porous portion.

2. The implantable medical device according to claim 1, wherein the thermoplastic composite body includes a superior-inferior axial stiffness relative to compression of less than 40 kN/mm.

3. The implantable medical device according to claim 1, wherein the at least one dense portion is continuous through a thickness dimension from the superior surface of the thermoplastic composite body to the inferior surface of the thermoplastic composite body.

4. The implantable medical device according to claim 1, wherein the at least one porous portion is continuous through the thickness dimension from the superior surface of the thermoplastic composite body to the inferior surface of the thermoplastic composite body.

5. The implantable medical device of claim 1, wherein the first thermoplastic polymer matrix and the second thermoplastic polymer matrix each includes a thermoplastic polymer material independently selected from the group consisting of polyaryletherketone, polyetheretherketone, polyetherketonekteone, polyetherketone, polyethylene, high density polyethylene, ultra-high molecular weight polyethylene, low density polyethylene, polyethylene oxide, polyurethane, polypropylene, polypropylene oxide, polysulfone, polyethersulfone, polyphenyl sulfone, polymethylmethacrylate, poly(DL-lactide), poly(L-lactide), poly(glycolide), poly(ε-caprolactone), poly(dioxanone), poly(glyconate), poly(hydroxybutyrate), poly(hydroxyvalerate, poly(orthoesters), poly(carboxylates), poly(propylene fumarate), poly(phosphates), poly(carbonates), poly(anhydrides), poly(iminocarbonates), poly(phosphazenes), polyacrylics from bisphenol monomers, hydroxypropylmethacrylate (bis-GMA), tri(ethylene glycol) dimethacrylate, copolymers thereof, and blends thereof.

6. The implantable medical device according to claim 5, wherein the first thermoplastic polymer matrix is polyaryletherketone and the second thermoplastic polymer matrix is polyaryletherketone.

7. The implantable medical device of claim 5, wherein the thermoplastic polymer material of the first thermoplastic polymer matrix is distinct from the thermoplastic polymer material of the second thermoplastic polymer matrix.

8. The implantable medical device of claim 1, wherein the thermoplastic composite body further includes at least one reinforcement material dispersed throughout at least one of the at least one dense portion and the at least one porous portion, the at least one reinforcement material being selected from the group consisting of hydroxyapatite, calcium-deficient hydroxyapatite, carbonated calcium hydroxyapatite, beta-tricalcium phosphate (beta-TCP), alpha-tricalcium phosphate (alpha-TCP), amorphous calcium phosphate (ACP), anisometric calcium phosphate, octacalcium phosphate (OCP), tetracalcium phosphate, biphasic calcium phosphate (BCP), anhydrous dicalcium phosphate (DCPA), dicalcium phosphate dihydrate (DCPD), anhydrous monocalcium phosphate (MCPA), monocalcium phosphate monohydrate (MCPM), glasses and glass-ceramics comprising $SiO_2$, CaO, $Na_2O$ and/or $P_2O_5$, and combinations thereof includes a plurality.

9. The implantable medical device of claim 1, wherein the at least one porous portion includes at least one porous outer wall disposed along at least one of the anterior surface of the thermoplastic composite body, the first lateral surface of the thermoplastic composite body, the second lateral surface of the thermoplastic composite body, or the posterior surface of the thermoplastic composite body.

10. The implantable medical device of claim 9, wherein the at least one porous portion further includes at least one porous central portion, and the at least one dense portion includes at least one dense core disposed between the at least one porous central portion and the at least one porous outer wall.

11. The implantable medical device of claim 1, wherein the thermoplastic composite body includes at least one central through cavity extending from the superior surface of the thermoplastic composite body to the inferior surface of the thermoplastic composite body and disposed inward from the anterior surface of the thermoplastic composite body, the first lateral surface of the thermoplastic composite body, the second lateral surface of the thermoplastic composite body, and the posterior surface of the thermoplastic composite body.

12. The implantable medical device of claim 11, wherein the at least one porous portion includes at least one porous central portion, and the at least one porous central portion defines an outer boundary of the at least one central through cavity.

13. The implantable medical device of claim 1, wherein the thermoplastic composite body lacks a central through cavity extending from the superior surface of the thermoplastic composite body to the inferior surface of the thermoplastic composite body and disposed inward from the anterior surface of the thermoplastic composite body, the first lateral surface of the thermoplastic composite body, the second lateral surface of the thermoplastic composite body, and the posterior surface of the thermoplastic composite body.

14. The implantable medical device of claim 1, wherein the at least one dense portion extends along at least one of the anterior surface of the thermoplastic composite body, the first lateral surface of the thermoplastic composite body, the second lateral surface of the thermoplastic composite body, or the posterior surface of the thermoplastic composite body, forming at least one dense edge.

15. The implantable medical device of claim 1, wherein the at least one dense portion forms at least one dense outer wall disposed along each of the anterior surface of the thermoplastic composite body, the first lateral surface of the thermoplastic composite body, the second lateral surface of the thermoplastic composite body, and the posterior surface of the thermoplastic composite body, and the at least one porous portion is disposed inward of the at least one dense outer wall.

16. The implantable medical device according to claim 1, wherein the at least one dense portion includes a plurality of projections extending outward relative to the at least one porous portion from at least one of the superior surface of the thermoplastic composite body or the inferior surface of the thermoplastic composite body.

17. The implantable medical device according to claim 1, wherein the at least one dense portion lacks any projections extending outward relative to the at least one porous portion from the superior surface of the thermoplastic composite body or the inferior surface of the thermoplastic composite body.

18. The implantable medical device according to claim 1, wherein the at least one porous portion forms the anterior surface of the thermoplastic composite body, the first lateral surface of the thermoplastic composite body, the second lateral surface of the thermoplastic composite body, and the posterior surface of the thermoplastic composite body, and the at least one dense portion includes a plurality of dense cores, each of the plurality of dense cores being disposed at vertices between each of the anterior surface of the thermoplastic composite body, the first lateral surface of the thermoplastic composite body, the second lateral surface of the thermoplastic composite body, and the posterior surface of the thermoplastic composite body.

19. A thermoplastic composite body including:
an anterior surface of the thermoplastic composite body;
a first lateral surface of the thermoplastic composite body;
a second lateral surface of the thermoplastic composite body;
a posterior surface of the thermoplastic composite body;
a superior surface of the thermoplastic composite body;
an inferior surface of the thermoplastic composite body;

at least one dense portion formed of a first thermoplastic polymer matrix that is essentially non-porous, and which is continuous through a thickness dimension from the superior surface of the thermoplastic composite body to the inferior surface of the thermoplastic composite body; and at least one porous portion formed of a porous thermoplastic polymer scaffold, the porous thermoplastic polymer scaffold being formed of a second thermoplastic polymer matrix, the at least one porous portion being continuous through the thickness dimension from the superior surface of the thermoplastic composite body to the inferior surface of the thermoplastic composite body, wherein the at least one dense portion and the at least one porous portion are integrally formed such that the thermoplastic composite body is a single continuous article free of adhesive joints between the at least one dense portion and the at least one porous portion and free of mechanical joints between the at least one dense portion and the at least one porous portion.

20. The implantable medical device according to claim 19, wherein the first thermoplastic polymer matrix is polyaryletherketone and the second thermoplastic polymer matrix is polyaryletherketone.

* * * * *